US012230967B2

(12) United States Patent
Makell et al.

(10) Patent No.: US 12,230,967 B2
(45) Date of Patent: Feb. 18, 2025

(54) APPARATUSES, METHODS, AND SYSTEMS FOR SUSTAINABLE ENERGY MICROGRID MOBILE MEDICAL SOLUTIONS

(71) Applicant: SEWW Energy Inc., Charlotte, NC (US)

(72) Inventors: Kevon R. Makell, Charlotte, NC (US); Brian Johnson, Charlotte, NC (US); David R. Ellis, Charlotte, NC (US); Myron Williams, Charlotte, NC (US)

( * ) Notice: Subject to any disclaimer, the term of this patent is extended or adjusted under 35 U.S.C. 154(b) by 2067 days.

(21) Appl. No.: 14/920,743

(22) Filed: Oct. 22, 2015

(65) Prior Publication Data

US 2016/0118799 A1    Apr. 28, 2016

Related U.S. Application Data

(60) Provisional application No. 62/067,431, filed on Oct. 22, 2014.

(51) Int. Cl.
*H02J 3/38* (2006.01)
*H02J 3/32* (2006.01)
*H02J 7/35* (2006.01)

(52) U.S. Cl.
CPC .............. *H02J 3/381* (2013.01); *H02J 3/322* (2020.01); *A61B 2560/0214* (2013.01);
(Continued)

(58) Field of Classification Search
CPC .... H02J 3/381; H02J 3/322; H02J 7/35; H02J 2300/24; H02J 2300/28; H02J 2300/10;
(Continued)

(56) References Cited

U.S. PATENT DOCUMENTS 8,682,495 B2\* 3/2014 Carralero .................. G06F 1/26
700/286
2009/0012917 A1\* 1/2009 Thompson ............. G06Q 50/06
700/297

(Continued)

OTHER PUBLICATIONS

Integration of Energy Analytics and Smart Energy Microgrid into Mobile Medicine Operations for the 2012 Democratic National Convention. Peter W. McCahill et al. vol. 29, Iss 6, pp. 600-607, Dec. 12, 2014 (Year: 2014).\*

(Continued)

*Primary Examiner* — Lincoln D Donovan
*Assistant Examiner* — Alex W Lam
(74) *Attorney, Agent, or Firm* — NORTON ROSE FULBRIGHT US LLP

(57) ABSTRACT

A method for energy management in a mobile medical unit, including: using a microgrid assessment tool to capture both granular load profiles and power quality data for a mobile medical unit powered by a microgrid; modeling a plurality of scenarios, using the data captured by the microgrid assessment tool to determine hybrid power system optimization; and supplying power to the mobile medical unit from one or more of a plurality of energy sources in the hybrid microgrid based on the optimization results. The plurality of energy sources includes at least one renewable energy source and at least one non-renewable energy source. A mobile medical system that includes a mobile medical unit and a hybrid microgrid configured to provide power to the mobile medical unit. The hybrid microgrid includes a measurement, verification, and control module, at least one renewable energy source, at least one energy storage device, and a generator.

27 Claims, 18 Drawing Sheets

(52) U.S. Cl.
CPC .............. *H02J 7/35* (2013.01); *H02J 2300/24* (2020.01); *H02J 2300/28* (2020.01); *Y02E 10/56* (2013.01); *Y02E 10/76* (2013.01)

(58) Field of Classification Search
CPC ............... H02J 2300/40; H02J 2310/10; H02J 2310/23; A61B 2560/0214; Y02E 10/56; Y02E 10/76; Y02E 70/30
See application file for complete search history.

(56) References Cited

U.S. PATENT DOCUMENTS

| | | | | |
|---|---|---|---|---|
| 2012/0006873 | A1* | 1/2012 | Chinn | A61G 3/0866 224/545 |
| 2012/0101639 | A1* | 4/2012 | Carralero | H04L 67/12 700/286 |
| 2013/0082529 | A1* | 4/2013 | Wolter | H02J 3/005 307/46 |
| 2014/0200717 | A1* | 7/2014 | Tilley | G05F 1/67 700/275 |
| 2014/0300182 | A1 | 10/2014 | James | |

OTHER PUBLICATIONS

Carolinas MED-1 Going Green While Providing Care At DNC In Charlotte, Aug. 28, 2012, Lime Energy Company (lime-energy.com) (Year: 2012).*
Renewable and Sustainable Energy Reviews 13, Jose L. Bernal-Agustin et al., Jan. 21, 2009 (Year: 2009).*
Callaway et al., "Time for a revolution: smart energy and microgrid use in disaster response", Disaster Medicine and Public Health Preparedness, Jun. 2014, vol. 8, Issue 3, pp. 252-259, Abstract Only.
International Search Report and Written Opinion, mailed Feb. 12, 2016, for PCT International Application No. PCT/US2015/57022.

* cited by examiner

APPARATUSES, METHODS, AND SYSTEMS FOR SUSTAINABLE ENERGY MICROGRID MOBILE MEDICAL SOLUTIONS

CROSS-REFERENCE TO RELATED APPLICATION

This application claims priority under 35 U.S.C. § 119 to U.S. Provisional Patent Application No. 62/067,431, filed Oct. 22, 2014, the contents of which are incorporated by reference herein in their entirety.

FIELD

The present subject matter is directed generally to apparatuses, methods, and systems for deploying microgrid technology, and more particularly, to APPARATUSES, METHODS, AND SYSTEMS FOR SUSTAINABLE ENERGY MICROGRID MOBILE MEDICAL SOLUTIONS (hereinafter "SMMS").

BACKGROUND

There is an immediate need for access to sustainable power and healthcare in rural communities throughout the world. For example, prevention, triage, and containment strategies deployed by the U.S. Government (e.g. AFRICOM, USAID), United Nations Agencies (e.g. WHO), NGOs, and other organizations have focused on adding healthcare infrastructure, such as Ebola Treatment Units, in various rural communities in Africa. This infrastructure is predominantly powered by diesel fuel.

These strategies have not been sufficient in confronting Ebola and other emerging diseases in the rural communities where the spread of disease continues because of the lack of effective healthcare infrastructure, the lack of self-contained power supplies, and the abandonment of existing local clinics by infected or fearful healthcare workers.

In rural communities, many of those infected with a given disease are fleeing to urban centers, overwhelming existing urban healthcare and humanitarian resources. Many who make the journey are being turned away due to overcrowding and are consequently left to further spread the disease, increasing the risk of infection and death in the greater population.

Infectious diseases such as Ebola are placing huge burdens on families and communities in rural areas where an individual who contracts the disease may infect the rest of his or her family. For example, estimates of mortality rates from Ebola in a Liberian household has been estimated to be as high as 80%, wiping out two or three generations at a time. Children are left to fend for themselves as orphans, with little hope for rehabilitation and repatriation within their communities, thanks to the stigma of the disease. These conditions underscore the need for access to infrastructure, power, and healthcare solutions in these rural communities.

Access to reliable power and healthcare solutions is not an issue only in the developing world. Modern society is dependent upon consistent and reliable energy supplies. In particular, the provision of medical care—in both disaster and non-disaster settings—is highly reliant on large volumes of consistent, high quality power. Natural, manmade, and technological disasters often have dramatic effects on the energy infrastructure of affected communities. During the acute post-disaster phase, this results in a loss of local sustainment and response capabilities. As the response proceeds, significant resources must be dedicated solely to restoring power, importing fuel and managing energy utilization.

Mobile medical and disaster medical response has traditionally relied on diesel generators to supply power. While dependable and widely available, diesel generators have the obvious limitation of needing a steady supply of fuel and the significant drawback of producing copious amounts of local air pollution. In the resource-poor setting of a disaster, reliance on diesel fuel can hamper disaster operations significantly. Recent experience in the United States with hurricanes, tornados, flooding, and other natural disasters has demonstrated the fragility of both utilities and fuel supplies as millions have been left without heat and power and many communities have experienced rampant fuel shortages. There is a need for systems and methods of integrating more sustainable power sources to disaster relief, healthcare, and other critical operations.

SUMMARY

A method for energy management in a mobile medical unit, including: using a microgrid assessment tool to capture both granular load profiles and power quality data for a mobile medical unit powered by a microgrid; modeling a plurality of scenarios, using the data captured by the microgrid assessment tool to determine hybrid power system optimization; and supplying power to the mobile medical unit from one or more of a plurality of energy sources in the hybrid microgrid based on the results of the optimization. The plurality of energy sources includes at least one renewable energy source and at least one non-renewable energy source. A mobile medical system that includes a mobile medical unit and a hybrid microgrid configured to provide power to the mobile medical unit. The hybrid microgrid includes a measurement, verification, and control module, at least one renewable energy source, at least one energy storage device, and a generator.

BRIEF DESCRIPTION OF THE DRAWINGS

The accompanying drawings illustrate various non-limiting, example, inventive aspects of the SMMS.

DETAILED DESCRIPTION

Figure 1:
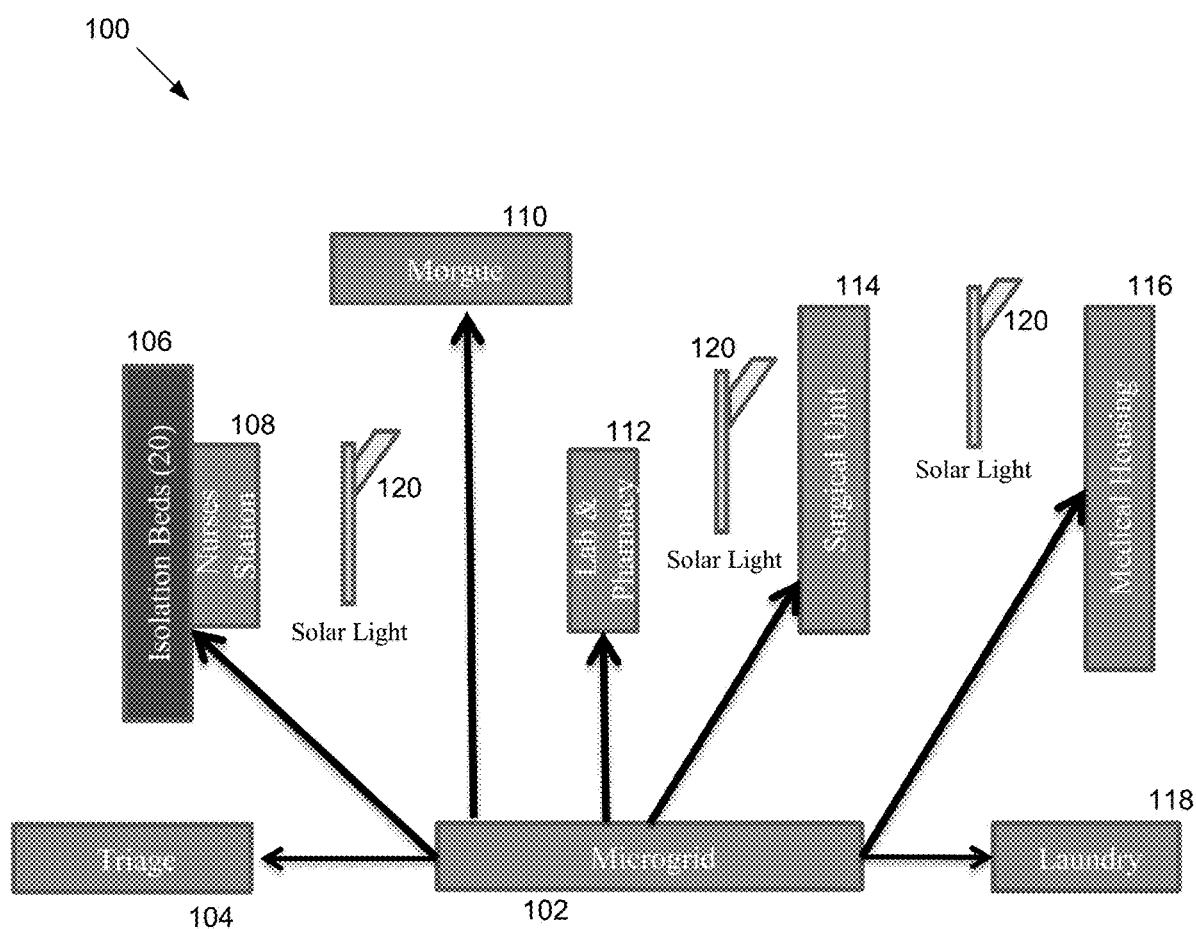
FIG. 1 is a schematic diagram showing one exemplary embodiment of the SMMS.

The APPARATUSES, METHODS, AND SYSTEMS FOR SUSTAINABLE ENERGY MICROGRID MOBILE MEDICAL SOLUTIONS ("SMMS") may include a fully integrated medical mobile solution that is tailored to the specific needs of the community being served. In one embodiment, the SMMS is made up of either ground units, container units, or a combination of both. The individual units may be powered with a sustainable, hybrid microgrid and configured to serve various purposes. For example, the ground units and container units may be configured to serve as laboratories, triage facilities, surgical units, morgues, and hospital-bed facilities, among other things. This solution is not only a short-term strategy for disaster-relief scenarios, but can also be adapted for the long term as part of a community's permanent infrastructure so that the people of the community will benefit long after their acute medical needs have been addressed.

The SMMS enables the extension of health services to remote and rural communities that have limited or no access to other medical care. In one implementation, this flexible and efficient solution offers access to healthcare on a continuing basis and provides service in times of emergency or natural disaster.

The SMMS integrates microgrid technology, reducing capital costs and fuel consumption versus standard solar powered units. The SMMS microgrid system more effectively captures and stores excess electricity produced by diesel generators, and also stabilizes the generator loading, which results in greater generator efficiency in converting diesel fuel to electricity. Additionally, the power quality delivered by the generator is stabilized, reducing the risk of damage to sensitive medical equipment. The SMMS also has the ability to integrate power from other sustainable sources (e.g. solar, wind, hydro, wave, geothermal, biomass, waste-to-energy, and others) which enables the diesel generator to be turned off periodically to conserve fuel. For example, this added efficiency can extend unit deployment time up to an additional eight days, with no additional fuel source consumption required.

The microgrid technology integrated into the SMMS addresses the need for security, reliability, efficiency, and affordability for a power supply. Microgrids offer local and transportable power generation from renewable energy and other distributed sources, with bulk powergrid interconnection capabilities. The SMMS may be configured for use in many different context, including to serve disaster recovery and emergency response needs, healthcare industry needs, utility and public infrastructure needs, and to provide smart energy management platforms for campus facilities. The SMMS may provide many benefits, including improved security and reliability of power supply and distribution, improved power quality and grid augmentation, and reduced energy and operating costs. The SMMS may also provide power source redundancy or serve as a primary power source, and may also provide an attractive return on investment, and reduce carbon dioxide and other greenhouse-gas emissions.

FIG. 1 is a schematic drawing showing one exemplary embodiment 100 of the SMMS, including a microgrid 102 providing power to a plurality of mobile units, including a triage center 104, an isolation unit 106 and nurses station 108, a morgue 110, a laboratory and pharmacy 112, a surgical unit 114, medical housing 116, and a laundry facility 118. A plurality of solar lighting fixtures 120, situated outside of the containers may also be powered by microgrid 102.

The SMMS may be configured to provide on-site medical care capabilities in rural communities thus alleviating the need for the infected to travel to urban centers for treatment. The SMMS can also provide rural point-of-contact facilities that greatly reduce the time to detection of infection and treatment for many diseases, which leads to better treatment outcomes and minimizes the spread of disease by minimizing contact between infected patients and the population at large. This has the added benefit of easing demands on urban-area healthcare resources. The SMMS can also be used to enhance existing medical facilities by deploying sustainable medical mobile solutions that expand the operational life of medical facilities and reduce obstacles associated with frequent fuel transport and rising fuel costs.

For communities with good access to roads, the SMMS may be deployed using mobile ground units. For communities with limited road access, the SMMS may be deployed using mobile container units. In one exemplary embodiment, the SMMS may also be used to retrofit existing healthcare infrastructure (clinics and/or Ebola Treatment Units, for example) with the provisions of specific units.

As explained above, these solutions can be configured for uses that include laboratories, triage areas, morgues, patient beds, housing for healthcare workers, and for any other suitable purpose. The SMMS may be customized to meet load demands; deliver secure and reliable power with hybrid sustainable microgrids using solar, wind, battery, and other renewable sources; convert diesel fuel to electricity and reduce overall diesel fuel consumption; and increase field operation time twofold over traditional power generators.

In one exemplary embodiment, the SMMS uses a hybrid microgrid with a 450 kWh battery bank and 13.5 kW photovoltaic array, which allows deployment operations time to be more than doubled before a generator needs to be refueled. For example, without the SMMS hybrid microgrid solution, a two-week deployment of a standard mobile medical unit might require 594,309 liters of diesel fuel at $1.21 per liter for a total cost $719,113. Integrating the SMMS hybrid microgrid solution decreases costs by half to $359,556. The SMMS may also provide fuel savings of 50% or more and decrease operations and maintenance costs that would otherwise be incurred due to less-than-ideal road conditions. The SMMS may also reduce the risk of exposure to relief personnel by limiting time in contaminated regions.

When an infectious disease outbreak occurs, the SMMS may be configured to assist in all stages of the disease management process, including identification and validation, isolation and containment, treatment and recovery, and rehabilitation and repatriation. In the identification and validation stage, lab and triage units of the SMMS may be configured to support rapid and accurate identification of the disease and to efficiently allocate limited medical resources in response to the disease. Data may also be collected to monitor viral mutations that could impact containment efforts.

In the isolation and containment stage, the SMMS may be configured to positively identify patients infected with the disease and isolate those patients in units according to the severity of their symptoms and the progression of the disease. The SMMS may be configured to address early-stage recovery needs as well as late-stage hospice needs. The SMMS may also include a morgue, where the deceased may be placed in isolated refrigeration units until safe and permanent disposal can occur.

In the treatment and recovery stage, the SMMS may be configured to enable effective treatment of illness, including both illnesses related to the infectious disease being treated, and other illnesses for which the ailing are seeking treatment. The SMMS may also be configured to provide lab certification and documentation to identify survivors who are free of the infectious disease so that these survivors can safely reenter society.

In the rehabilitation and repatriation stage, the SMMS may become part of the permanent infrastructure of the community and be used on a long-term basis for various needs, including ongoing healthcare services, housing for those disenfranchised by the disease, and for schooling. Medical and other personnel may train local community members so that those local community members can maintain the new infrastructure provided by the SMMS.

Figure 2:
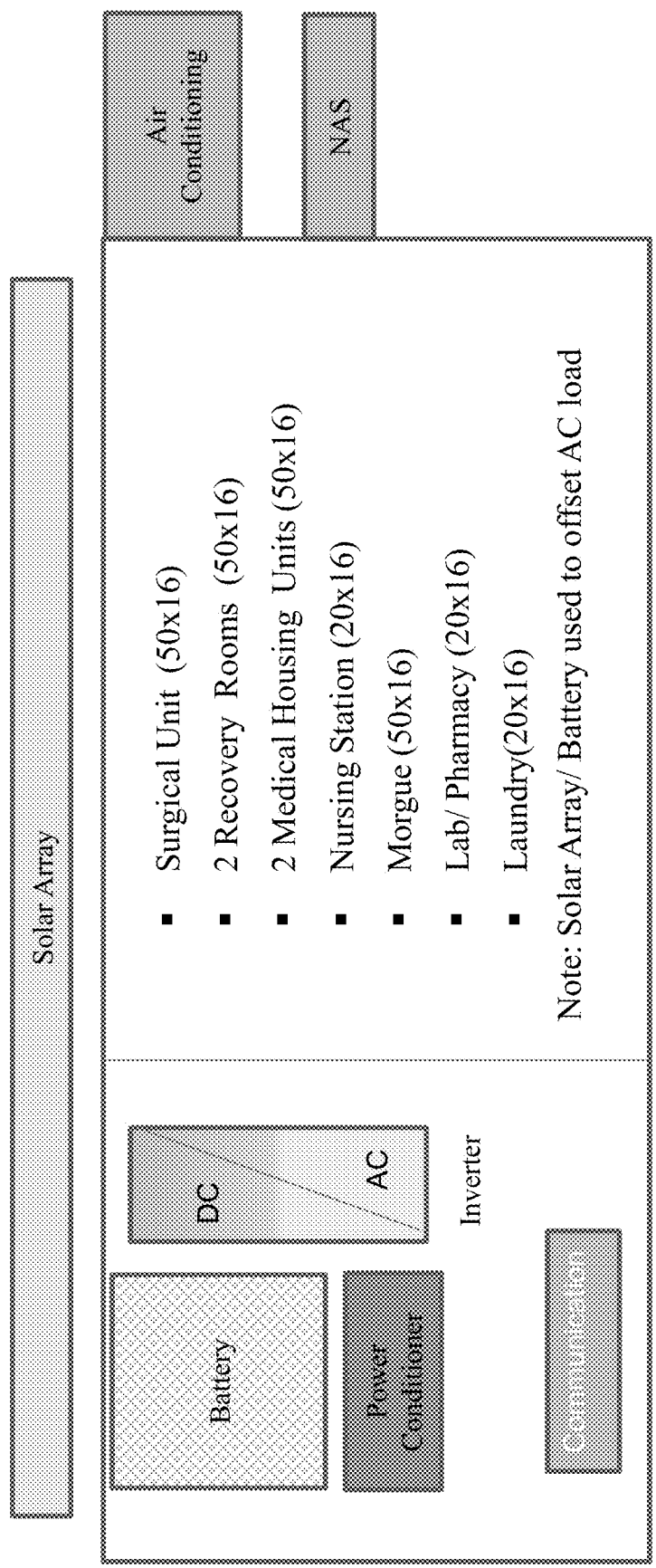
FIG. 2 is a schematic diagram illustrating power delivery for an individual unit of an exemplary embodiment of the SMMS.
Figure 3:
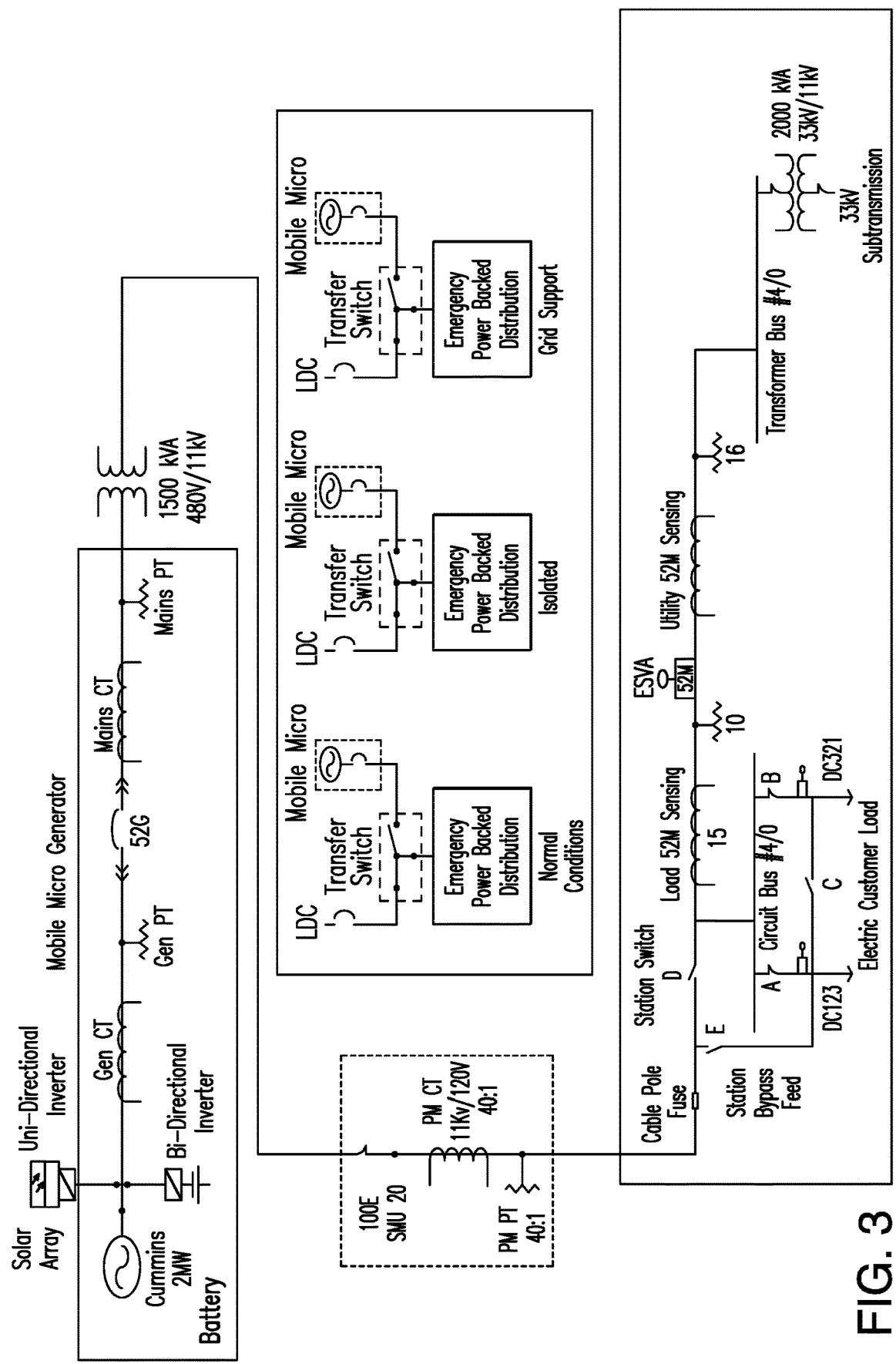
FIG. 3 is a circuit diagram illustrating the power delivery for an individual unit of an exemplary embodiment of the SMMS.

FIG. 2 is a schematic diagram illustrating the power delivery for an individual unit of an exemplary SMMS. In one exemplary embodiment, the individual unit may include a solar array, a battery, a power conditioner, an inverter, a communication module, an air conditioner, and an NAS module. As described above, the unit may be configured to be used for medical purposes or any other suitable purpose, including as a surgical unit, a recovery room, medical housing units, a nursing station, a morgue, a lab, a pharmacy, and a laundry. FIG. 3 is a circuit diagram illustrating the power delivery for an individual unit of an exemplary SMMS.

Figure 4:
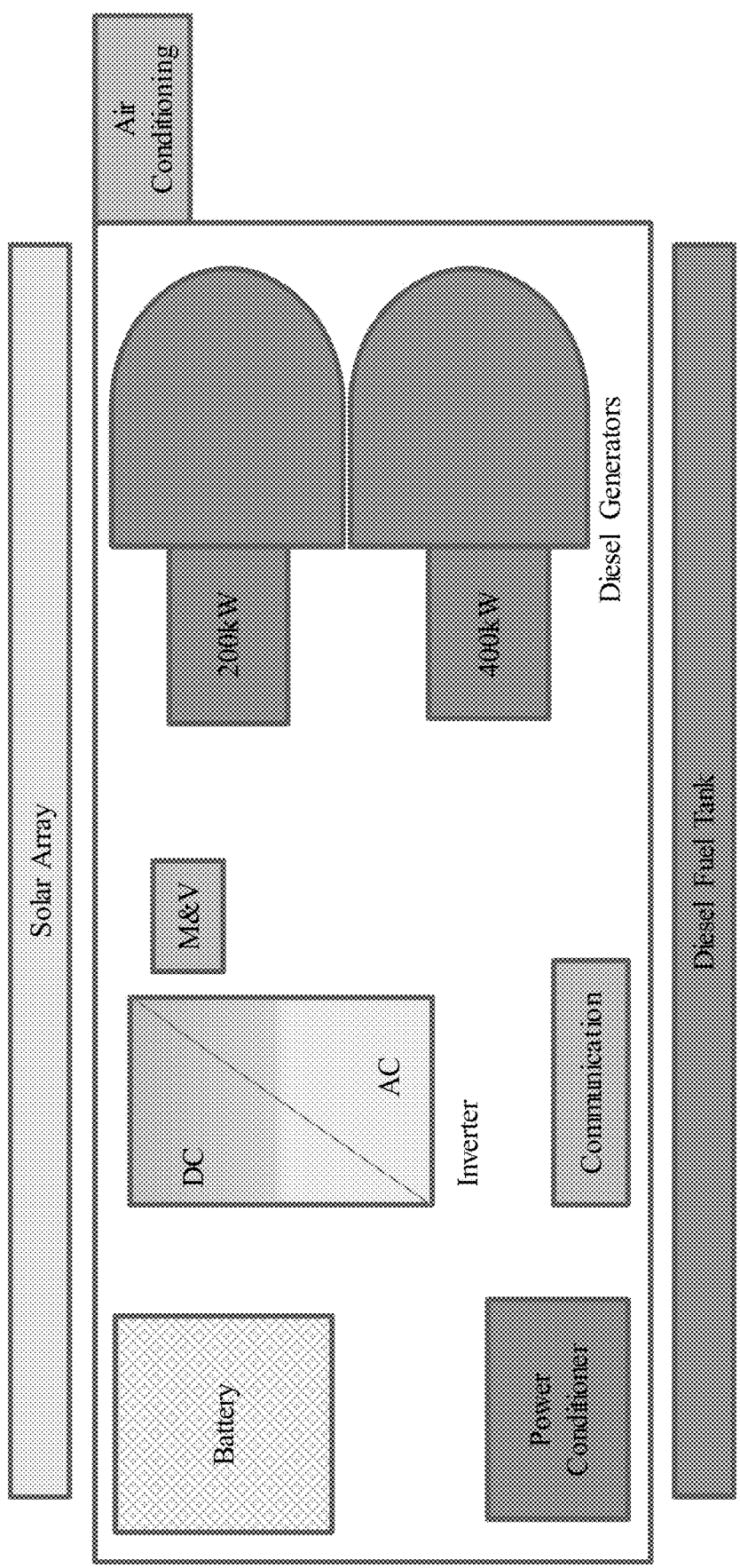
FIG. 4 is a schematic diagram illustrating the microgrid supplying power to the units in one exemplary embodiment of the SMMS.
Figure 5:
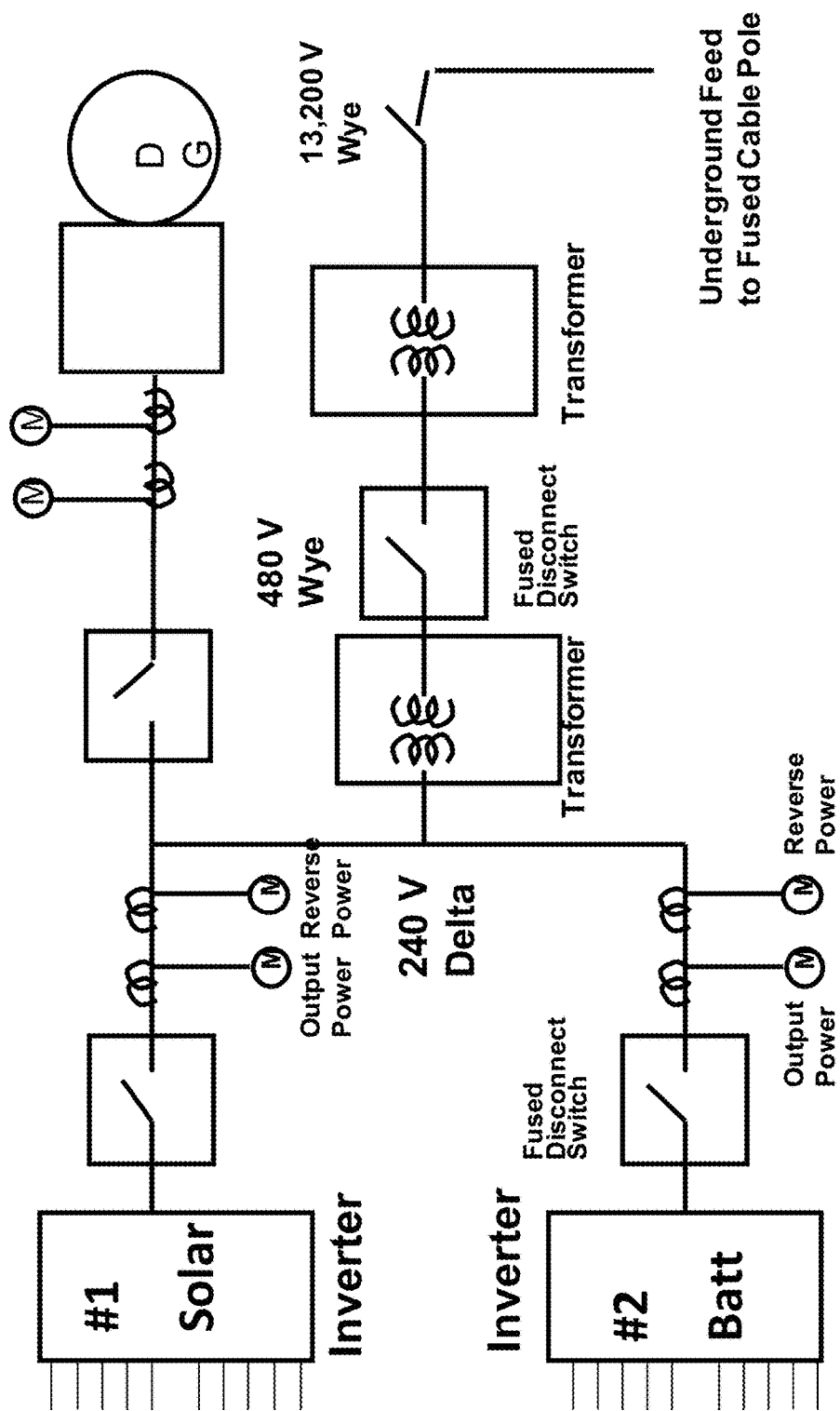
FIG. 5 is a circuit diagram illustrating an exemplary microgrid in one embodiment of the SMMS.
Figure 6:
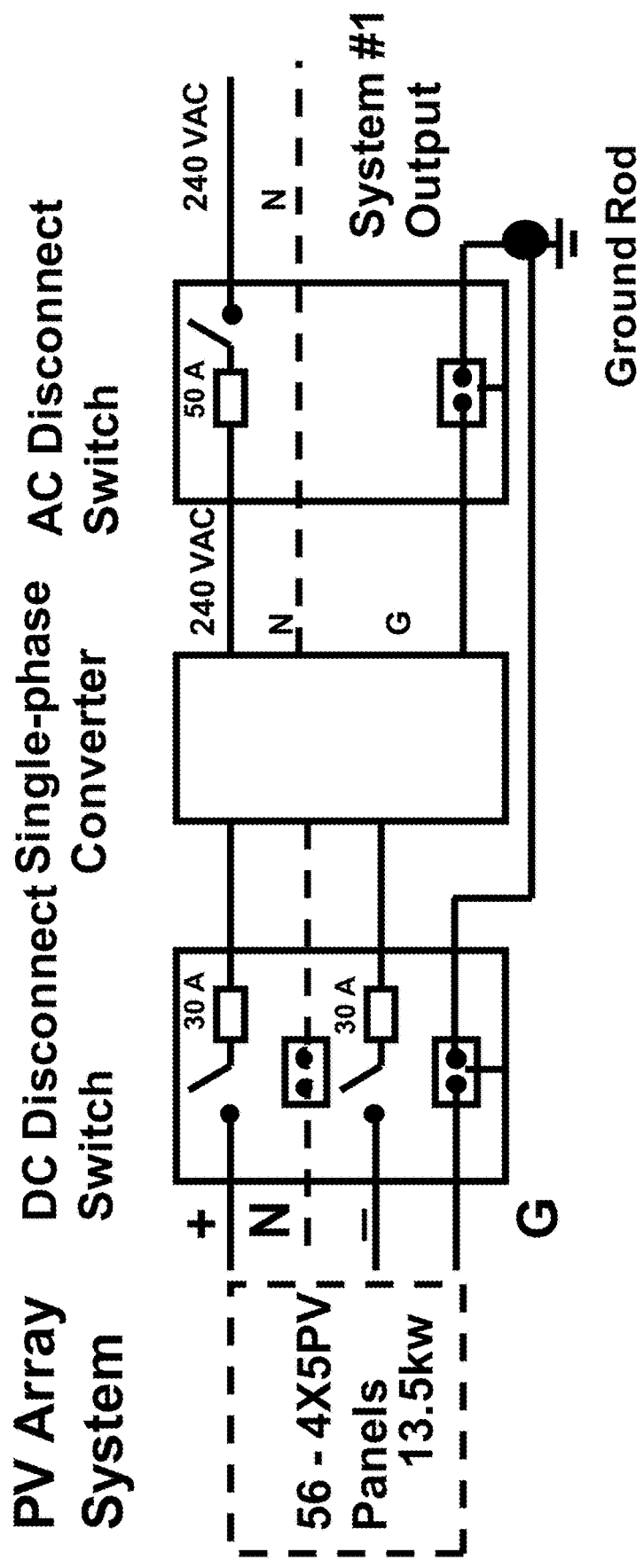
FIG. 6 is a circuit diagram illustrating an exemplary photovoltaic solar array system that may be used with an exemplary microgrid in one embodiment of the SMMS.
Figure 7:
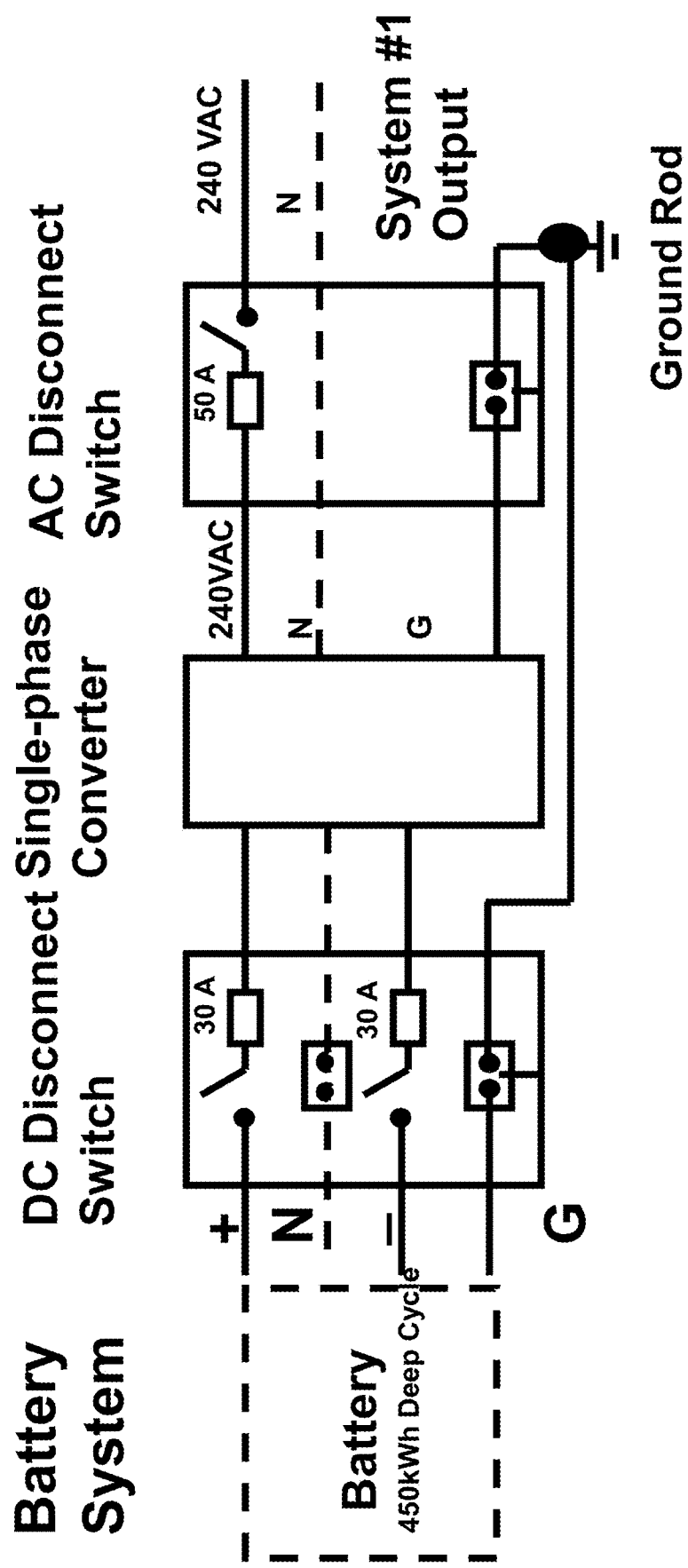
FIG. 7 is a circuit diagram illustrating an exemplary battery system that may be used with an exemplary microgrid in one embodiment of the SMMS.

FIG. 4 is a schematic diagram illustrating the microgrid supplying power to the units in one exemplary embodiment of the SMMS. In one embodiment, the microgrid is a hybrid microgrid, meaning that it provides power using fuel sources, such as diesel fuel, as well as sustainable-energy sources such as solar and wind power, and battery sources. In the embodiment shown, the microgrid includes a battery, a power conditioner, an inverter, a measurement and verification (M&V) module, a photovoltaic solar array, an air conditioning unit, and one or more diesel generators connected to a diesel fuel tank. In one embodiment, the microgrid may also include a control module integrated with or interfacing with the measurement and verification module. FIG. 5 is a circuit diagram illustrating an exemplary microgrid of the SMMS having both a solar energy source, such as a photovoltaic solar array, and a battery. FIG. 6 is a circuit diagram illustrating an exemplary photovoltaic solar array system that may be used with the microgrid of the SMMS. FIG. 7 is a circuit diagram illustrating an exemplary battery system that may be used with the microgrid of the SMMS.

Figure 8:
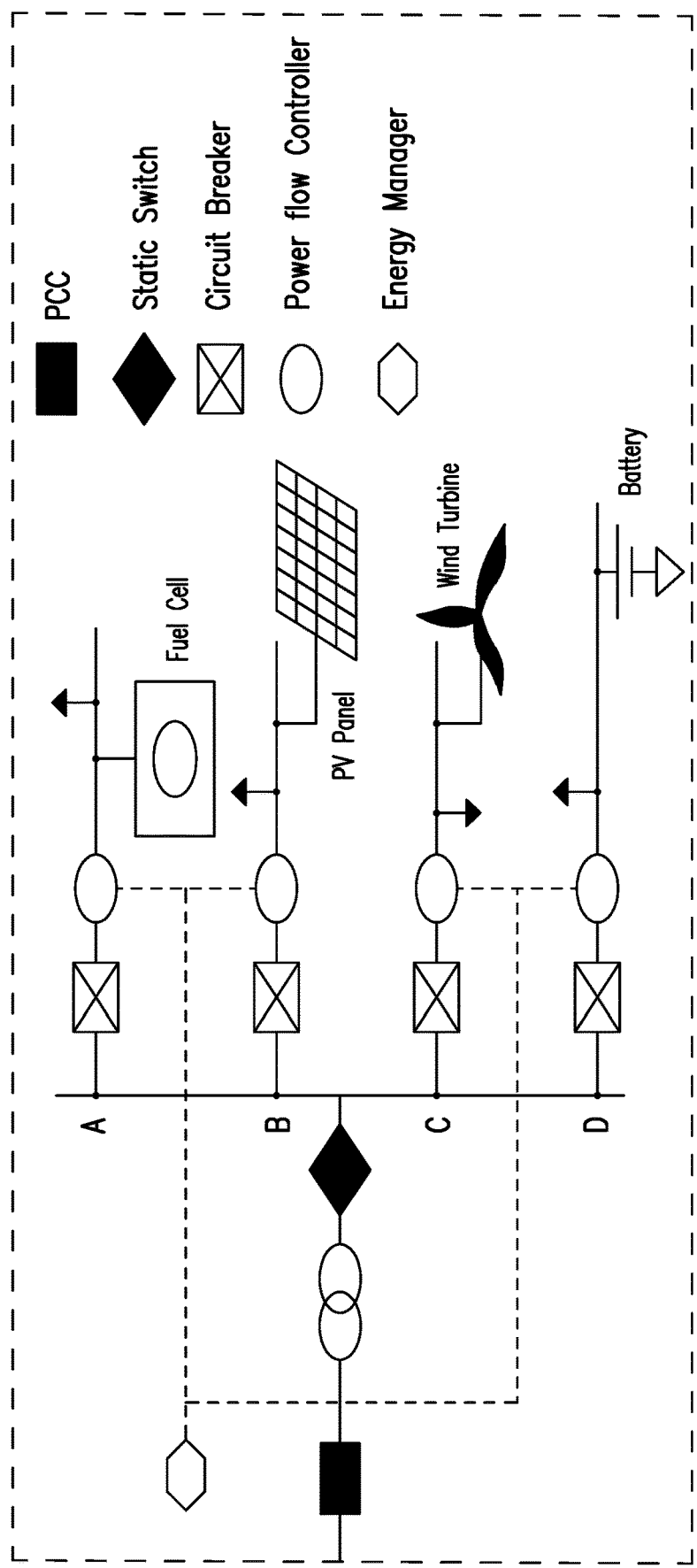
FIG. 8 is a schematic diagram illustrating another exemplary embodiment of a microgrid that may be used with the SMMS.

FIG. 8 is a schematic diagram illustrating another exemplary embodiment of a microgrid that may be used with the SMMS. As shown, the microgrid may include a fuel cell, a photovoltaic panel, a wind turbine, and a battery as sources of energy. The microgrid may also include a point of common coupling (PCC), a power flow controller, and an energy manager, along with a circuit breaker for each power source.

Figure 9:
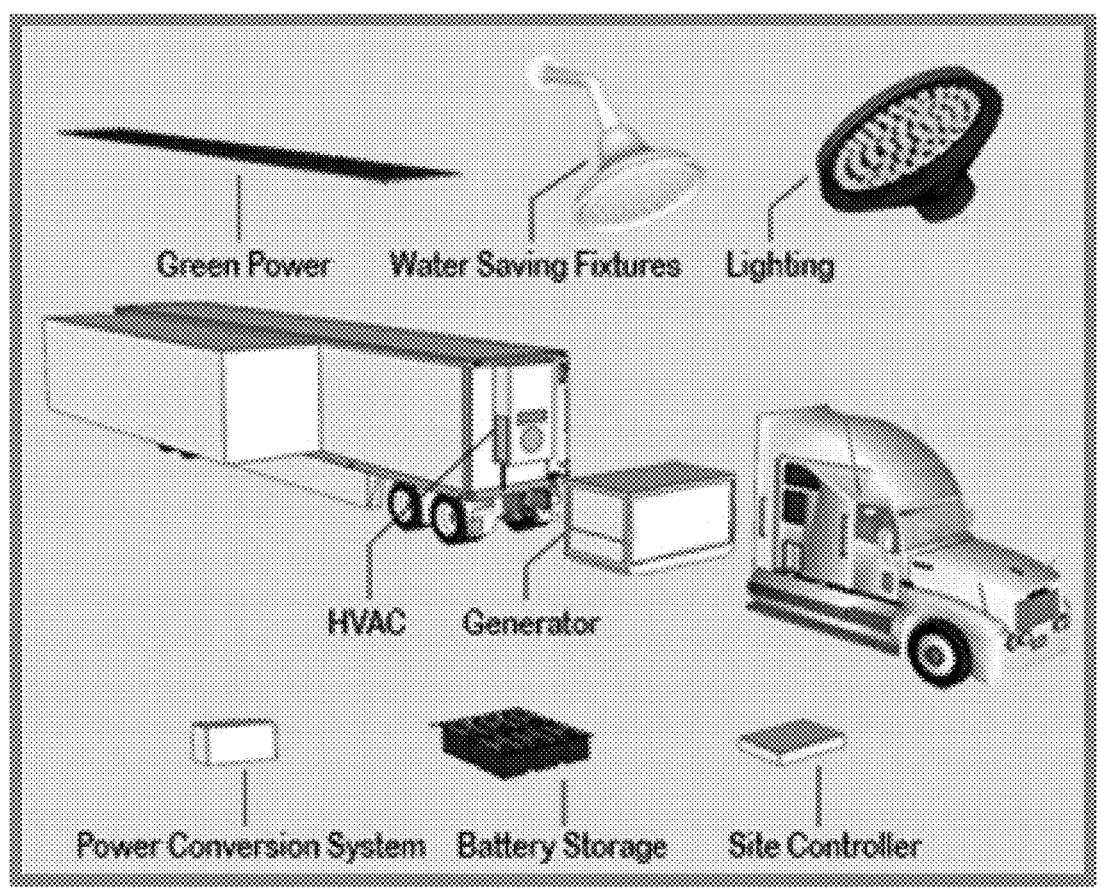
FIG. 9 shows exemplary embodiments of a mobile ground unit that may be used in one embodiment of the SMMS.

In one exemplary embodiment, the SMMS may include one or more mobile ground units, as illustrated in FIG. 9. In one embodiment, the mobile ground unit is integrated into a semi-truck trailer. The mobile ground unit may be deployed in locations with good road access, as it may be delivered using a semi-truck and a tractor trailer. In one exemplary embodiment the mobile ground unit includes a heating and air conditioning unit, a generator, a solar panel or other renewable energy source, a power conversion system, a battery storage unit, and site controller. The mobile ground unit may also include such features as water-saving fixtures and energy-efficient lighting fixtures. A plurality of mobile ground units may be employed in one embodiment of the SMMS to provide a full-service operating room, acute- and critical-care beds, a full-service pharmacy with refrigeration, water filtration, technology integration for remote health system access, video conferencing for telemedicine, and technology equipped classrooms for health education.

Figure 10:
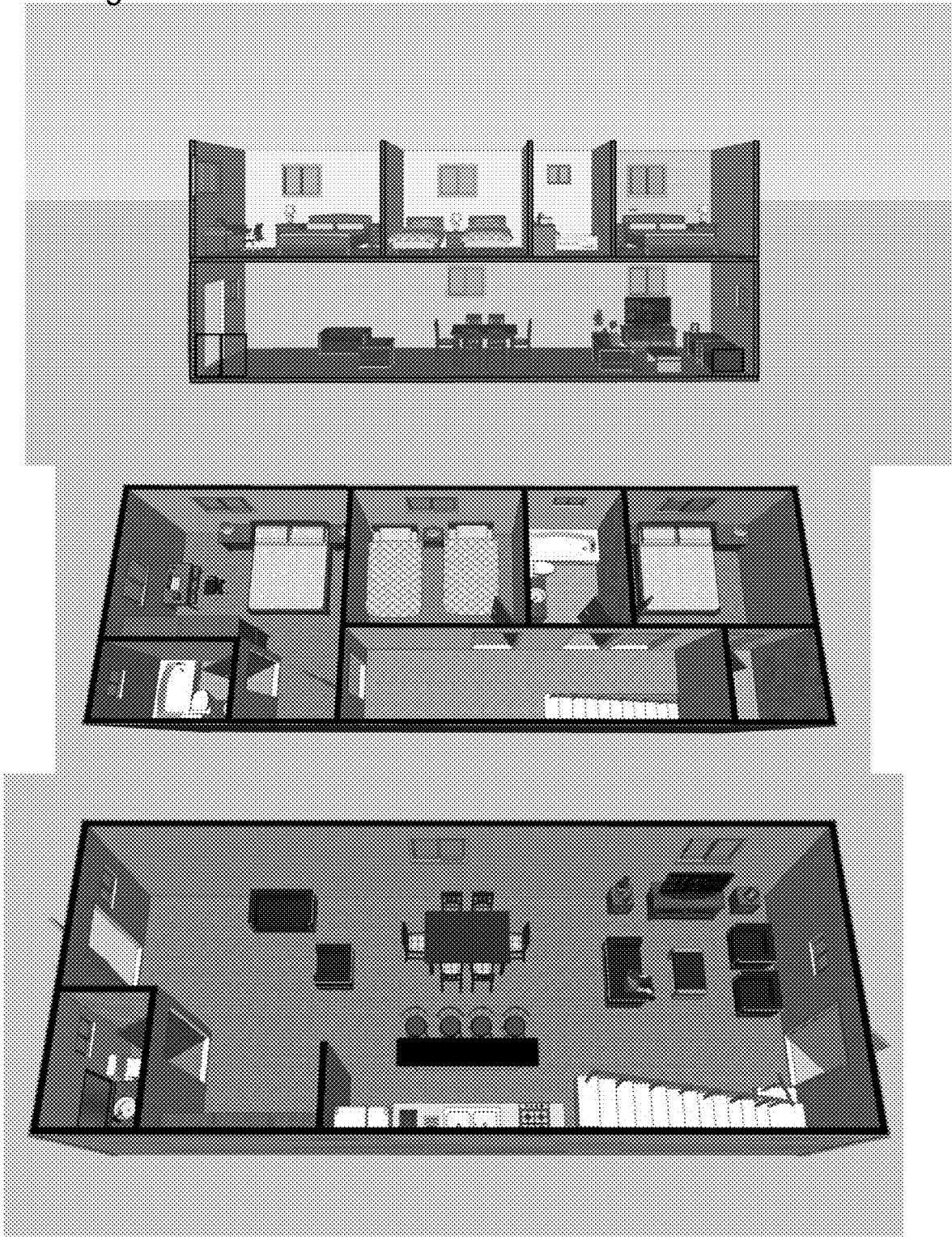
FIG. 10 is an illustration of a mobile unit configured to serve as housing for medical staff in an exemplary embodiment of the SMMS.
Figure 11:
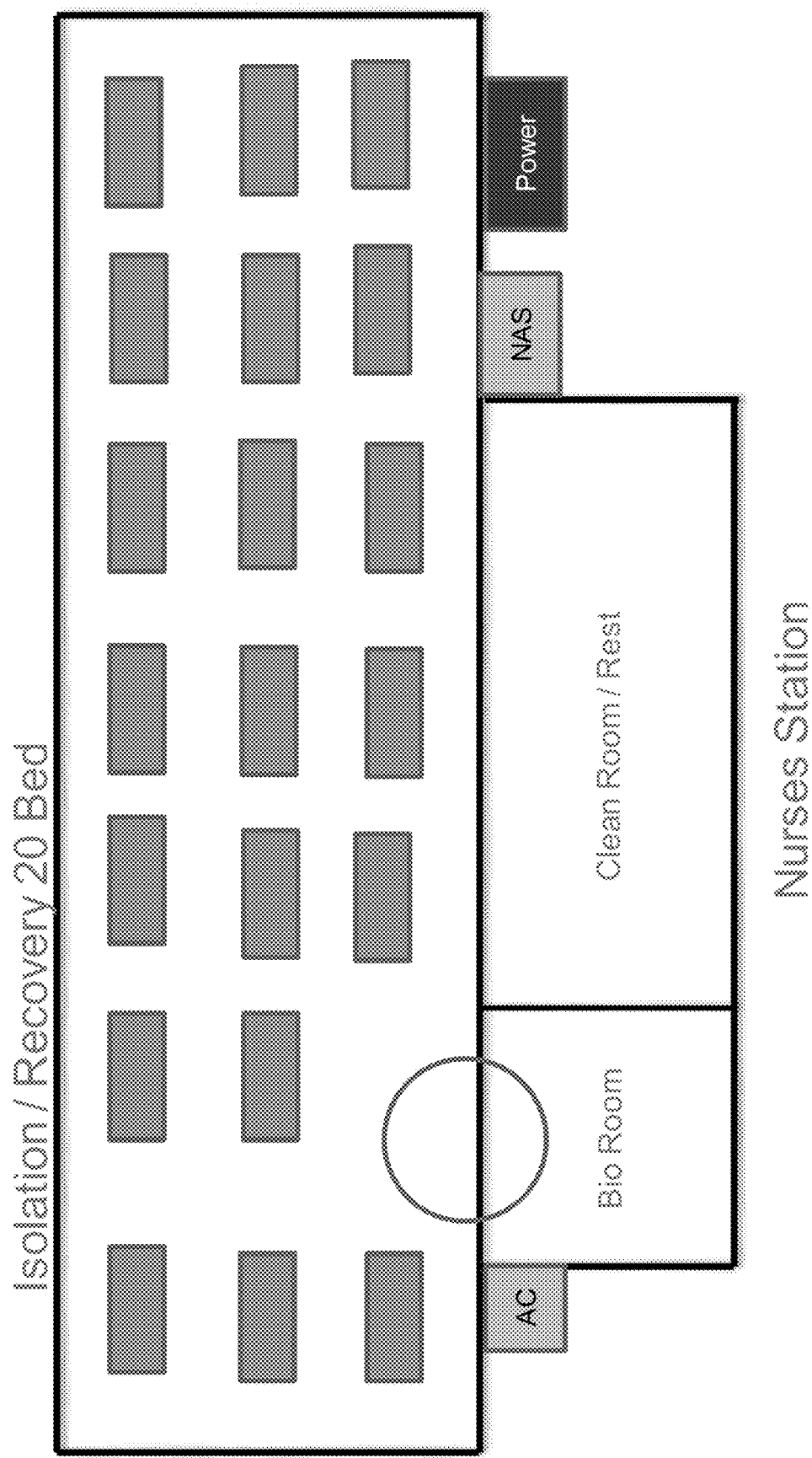
FIG. 11 illustrates an exemplary embodiment of a mobile unit in one implementation of the SMMS that has been configured as a patient-recovery facility.
Figure 12:
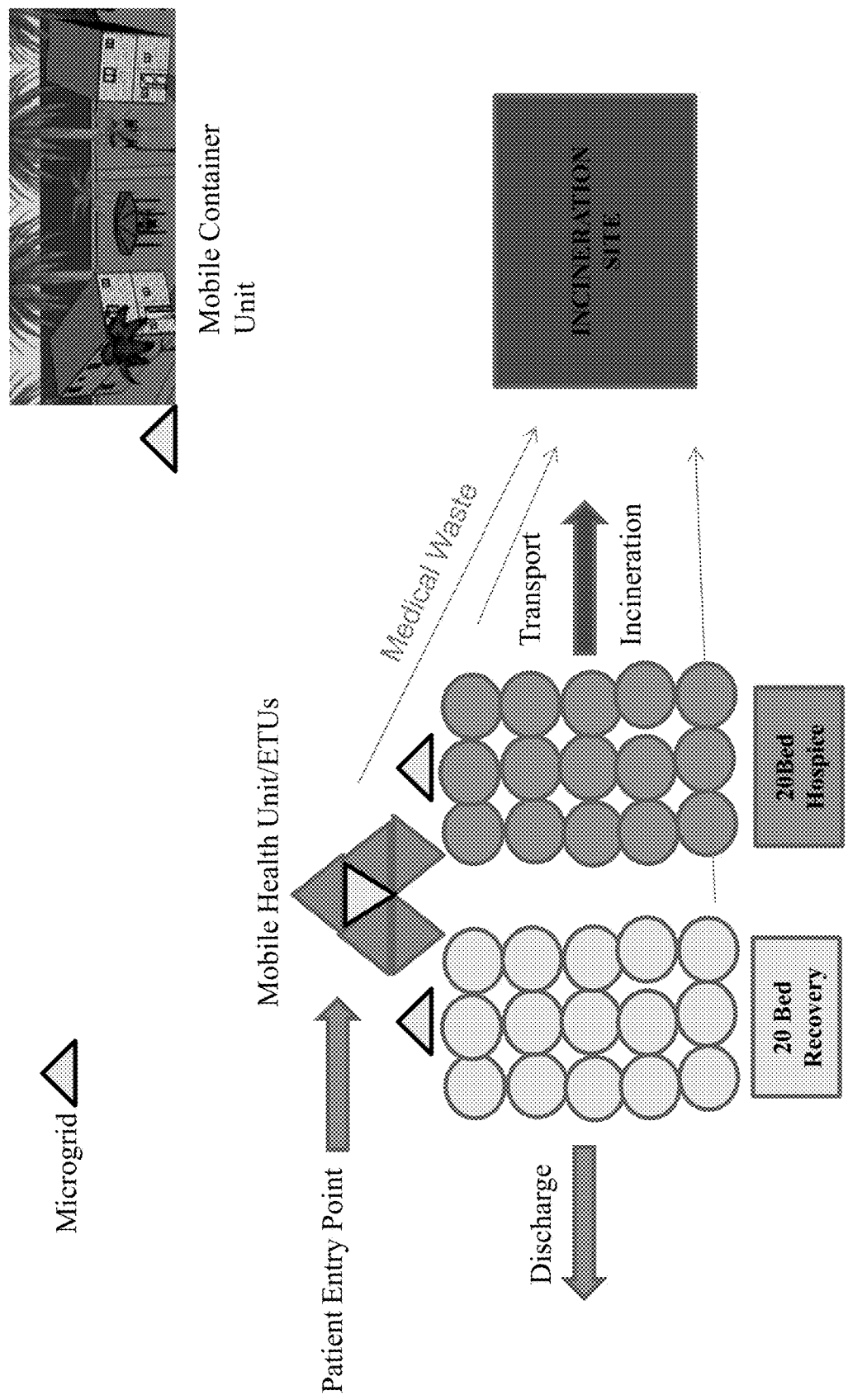
FIG. 12 is a schematic diagram illustrating an exemplary embodiment of the SMMS with a plurality of microgrids powering several mobile units.

In another exemplary embodiment the SMMS may include one or more mobile container units that are best suited for deployment in locations with limited or no road access. Mobile container units may be collapsible and stackable such that the units can be readily assembled on site. FIG. 10 is an illustration of a mobile unit, which could be either a mobile ground unit, or a mobile container unit, that has been configured to serve as housing for medical staff in an exemplary embodiment of the SMMS. FIG. 11 illustrates an exemplary embodiment of a mobile unit of the SMMS that has been configured as a patient-recovery facility with twenty beds, with a controlled-environment entrance that includes a bio room and a clean room. In one exemplary embodiment, the patient-recovery facility may be adjacent to or adjoining a nurses station. FIG. 12 is a schematic diagram illustrating an exemplary embodiment of the SMMS with a plurality of microgrids powering several mobile units, including a patient-recovery facility, a hospice facility, and an incineration cite.

In one exemplary embodiment, the SMMS may be configured to integrate distributed generation, high-efficiency batteries, and "smart" energy utilization in support of major out-of-hospital medical-response operations.

The SMMS, in one exemplary embodiment, may be a mobile medical facility composed of a fleet of vehicles and trailers that provides comprehensive medical-care capacities to support disaster response and special-event operations. The SMMS may be configured to deploy energy analytics and an energy microgrid in support of mobile clinical operations. Energy use data recorded at the mobile medical facility may then be analyzed to create energy utilization models that integrate advanced battery technology, solar photovoltaic and energy conservation measures to improve future disaster response operations.

In one exemplary embodiment, the generators that supply power for the SMMS may have a minimum loading ratio (MLR) of 30 kVA. This means that loads below 30 kW lead to diesel fuel consumption at the same rate as a 30 kW load. In one instance, testing data gathered from two training and support deployments of the SMMS showed the maximum load to be around 20 kW. This discrepancy in minimum loading ratio versus actual load leads to significant energy waste. The lack of an energy storage system reduces generator efficiency and limits integration of alternative energy generation strategies. A storage system also allows for alternative generation sources such as photovoltaics to be incorporated. Modeling with a 450 kWh battery bank and 13.5 kW PV array showed a twofold increase in potential deployment times using the same amount of fuel.

Testing has demonstrated that the incorporation of a microgrid energy management system and a modern battery system maximize the generators' output in the SMMS. For example, using a 450 kWh battery bank and 13.5 kW PV array, deployment operations time could be more than doubled before refueling. This marks a dramatic increase in patient-care capabilities and has significant public-health implications. These results highlight the value of the smart-microgrid technology of the SMMS in developing energy independent mobile medical capabilities and expanding cost-effective, high-quality medical response.

In one exemplary embodiment, the SMMS may include a mobile hospital fleet, such as the mobile hospital fleet operated by Carolinas HealthCare Systems, which includes a 53-foot modified long-haul trailer with diesel tractor trailer. The long-haul trailer serves as a climate controlled treatment facility with six intensive-care-unit beds, advanced cardiac monitoring, a functional operating room, and 14 total patient bays. The trailer is powered by 100 kVA, 208V 3-phase diesel generator. The fleet may also include an additional 53-foot modified long-haul trailer that acts as the primary supply vehicle and can transform to function as a berthing and command and control vehicle. The fleet may also include other vehicles, such as sport-utility vehicles to serve as supply vehicles and command-staff transport and response vehicles, and campers that may function as kitchen, dining, shower, laundry, and rest vehicles.

This exemplary embodiment of the SMMS is uniquely capable of providing comprehensive medical care in disaster-relief situations and mass-gathering public events. In one exemplary embodiment, the SMMS may be comprised of one treatment vehicle and six support vehicles that can provide advanced resources up to and including operative interventions, cardiac monitoring, portable radiology, and intensive care.

The SMMS may include improvements to a mobile medical fleet that would increase energy efficiency, decrease demands on diesel generators, and expand emergency medical care capabilities. The SMMS may also serve to increase operational independence, allowing for longer deployments in potentially more austere environments. Additional environmental and financial benefits include decreased emissions and expenses from fuel costs.

In one exemplary embodiment, the SMMS may be configured to conduct testing in two phases. The first phase may include the execution of an energy audit to quantify the energy usage of the SMMS and identify specific targets for improvement (HVAC, lighting, medical and clerical equipment, etc.). This energy audit is the first of its kind to quantify energy utilization in large-scale prehospital medical response. In initial testing, the energy audit revealed that the two 100 kVA, 208V 3 phase generators of the mobile medical fleet were operating at a low load capacity, below minimum efficiency, resulting in significant energy waste. As the power plant was already functioning below its optimum load, implementing energy conservation measures would reduce further the required generator output, but have no effect on fuel utilization. The energy audit demonstrated that if system generators could operate at an optimal load, they would increase power generation without any significant change in fuel consumption. The implementation of a microgrid in the SMMS addresses the increased generator efficiency while leveraging energy conservation measures.

The second phase of testing of the SMMS may include an investigation of the feasibility and potential benefit of implementing a microgrid to achieve this maximization in efficiency of the existing diesel generators. A microgrid is a localized grouping of electricity generation, energy storage, and loads, which allow a degree of independence from the centralized grid.

Incorporating migrogrids into mobile medical fleets offers several benefits. First, it allows for the possibility of distributive energy generation. Distributive generation allows for multiple energy sources to be harnessed and integrated into a single energy system. With a distributive generation system, alternate sources such as solar and wind may be added to the fleet to further decrease the demands on the diesel generators. Secondly, it allows integration of an energy storage system (e.g. batteries). For example, in one exemplary embodiment, the SMMS includes a comprehensive battery array that enables the generators to operate at their maximum efficient load by diverting "surplus" power into the storage system. The SMMS can then be configured to alternately operate off the batteries and the generators, meaning the generators can be intermittently shut down creating a substantial fuel savings. In addition, a microgrid offers conditioned power. The electricity produced by the diesel generators is highly variable. A power conditioner provides increased power quality meaning less variation in voltage magnitude, less transient changes in voltages and currents, and improved harmonic content in the alternating current (AC) waveform. Improved energy quality extends the lifetime of the sensitive electronic equipment such as mechanical ventilators, cardiac monitors, and computer systems employed during patient care in the SMMS. A detailed load analysis of the mobile hospital was performed and the data was used for microgrid modeling. The data was used to model different power system configurations to determine the optimal microgrid design for use in the SMMS. Further details of this load analysis is described below.

Figure 13:
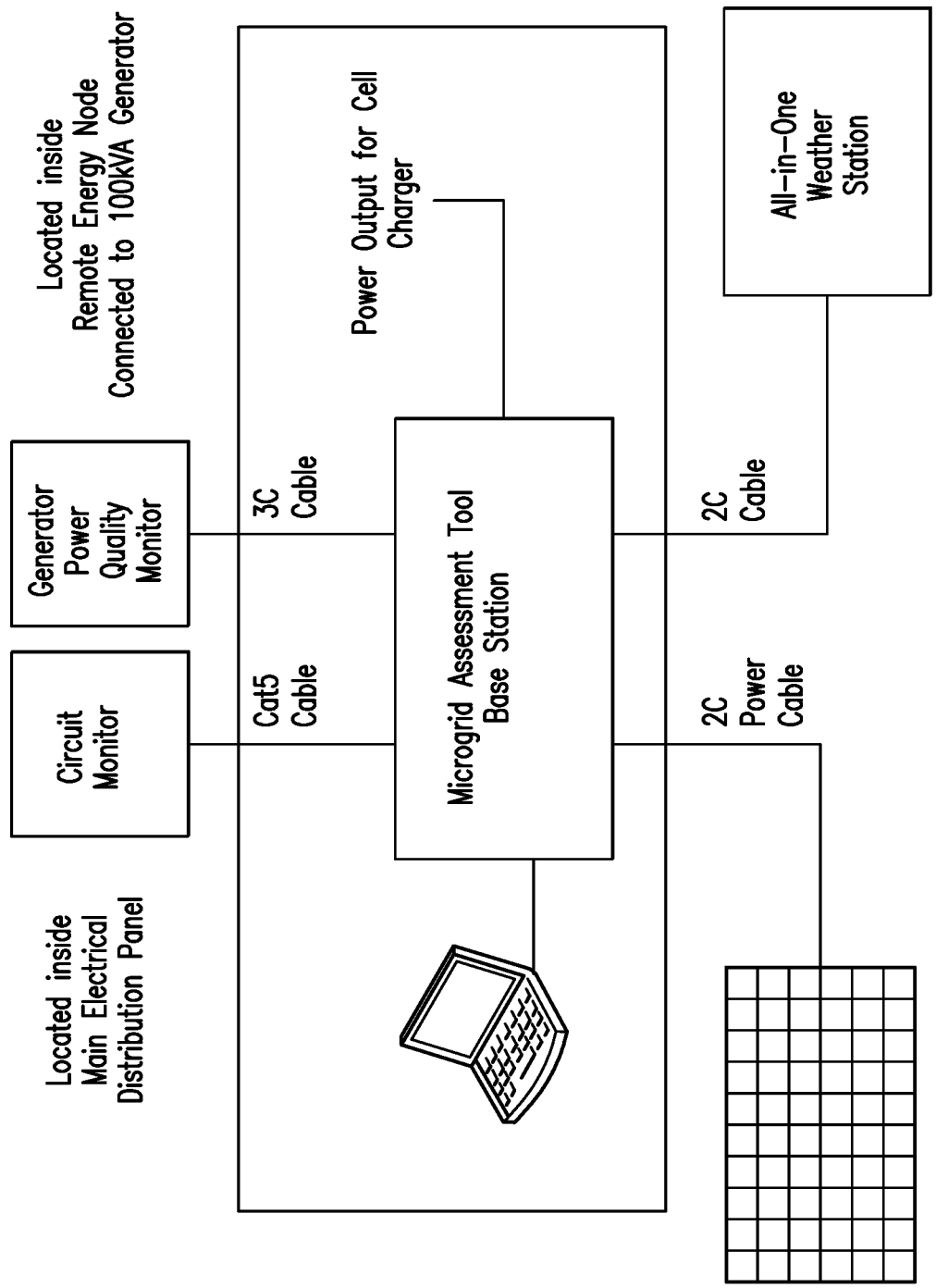
FIG. 13 is a diagram of an exemplary microgrid assessment tool that may be used in one implementation of the SMMS.

In one exemplary embodiment, a Microgrid Assessment Tool (MAT) may be used to capture both granular load profiles and the power quality for use in a microgrid feasibility report. FIG. 13 shows a diagram of the MAT. In one exemplary embodiment, the MAT may include a base station with an embedded datalogger; an absorbed glass mat battery and photovoltaic module for charging the battery; a circuit level monitor with a plurality of current transformers and voltage sensors for each of the three phases installed in the main load panel; a power quality meter with three split-core current transformers for measuring generator output before any loads; and a weather station that included a second-class pyranometer for measuring solar resource and an all-in-one weather station and transmitter configured to measure and transmit wind speed, wind direction, precipitation, ambient temperature, relative humidity, barometric pressure, and any other relevant metric. The circuit level monitor may be used to measure the three input phases of the main load panel, six circuits that power the three-phase HVAC units, and three additional circuits for lights and plug loads.

In one exemplary embodiment, the SMMS may be configured to model several scenarios using a hybrid power system optimization. The parameters considered may include photovoltaic array size, power converter capacity, battery bank size, different load profile scenarios, generator minimum load ratio, efficiency, and solar resource available.

In one exemplary embodiment, Photovoltaic (PV) arrays of 0, 4.5, 9 and 13.5 kW may be modeled. In one embodiment of the SMMS, PV arrays may be added to the top of each tractor trailer. Once capacity has been reached, any additional PV generation could also be added to other structures, for example, via portable ground-mount arrays assembled on site or thin-film modules integrated into tents or other structures.

Power converters may be required when interfacing Alternating Current (AC) generation and loads and Direct Current (DC) generation sources and battery storage. The diesel generators are AC generation and photovoltaic arrays are DC generation. The power converter charges the batteries from the generator and inverts the DC power from the batteries for use in AC loads. Most medical and consumer electronic equipment deployed in mobile medical units is designed to operate off an AC source.

The rate at which a diesel generator consumes fuel depends on the loading ratio. This loading ratio is defined as the load divided by the rated generator capacity. A fuel consumption chart, for example, the chart published by Diesel Service & Supply Inc. of Brighton, CO, may be used to estimate the generator fuel consumption of the SMMS microgrid based on generator loading. For example, the chart shows consumption rates for 25%, 50%, 75% and full load as 2.6, 4.1, 5.8 and 7.4 gal/hour respectively.

In one exemplary embodiment of the SMMS, there are generator controls that set the minimum loading at which the fuel consumption remains constant to ensure full fuel combustion and reliable generator operation under low load conditions. This translates to a point on the fuel consumption curve which is referred to as the generator's minimum loading ratio (MLR). Below the MLR, any decreases in the load no longer correspond to decreases in fuel consumption. In one embodiment, this parameter may be set to 30% in the software analytic model. This translates to 30 kVA for the generator of the SMMS. In this case, loads of 10 kW, 20 kW and 28 kW all consume the same amount of fuel as a 30 kW load.

The model is most sensitive to the generator MLR parameter because of the low loading of the generator relative to its rated capacity. In one embodiment, a sensitivity analysis may be performed by modeling the MLR for the generator at 30% and 15%.

In one embodiment, batteries may be modeled to estimate fuel savings due to energy storage. For example, the commonly used Surrette KSP25P battery may be modeled configured in 48V strings. Since each battery is 4V, there are 12 batteries in each serial string. Higher battery bank voltages could be used to save on conductor costs, but the modeling results would not change significantly. The 4KS25Ps are 1900 Ah lead-acid batteries that weigh 315 lbs each.

In one exemplary embodiment, a range of battery-bank sizes may be modeled for energy storage. Three battery-bank sizes may be reported for comparison—no battery bank, small, and large. The small bank may consist of a single battery string of 12 batteries with a total capacity of 90 kWh and may be the smallest battery bank string at 48V using the selected batteries. In one embodiment, the large bank may consist of 5 strings with 60 batteries and a 450 kWh capacity and may be the largest battery bank that could be supported using the weight capacity rating of a standard 20' trailer using an advanced battery technology. Advanced battery technologies such as Lithium Ion batteries can decrease the weight of the battery bank by three times and can decrease the volume by nearly six times.

The effect of energy efficiency may also be modeled using an efficiency inputs parameter in the load profiles. In one embodiment, energy efficiency measures can be assumed to be able to decrease total usage by 25%, based on data collected from the energy audit. Described areas of potential improvement include a more efficient HVAC system, envelope sealing, LED light bulbs and some type of real-time display for displaying electrical loads to inspire behavioral modifications.

In one exemplary embodiment, the SMMS may operate in one of two modes: event-support mode and disaster-relief mode. In event-support mode, the hospital may be fully staffed for only a fraction of the day, for example, during daytime hours. In such a case, the load profile would reflect this usage pattern with higher consumption during the day and lower consumption at night when the heating load is decreased by the sun not heating the exterior of the unit and a decreased internal heat loading by limited staff occupancy.

Figure 14:
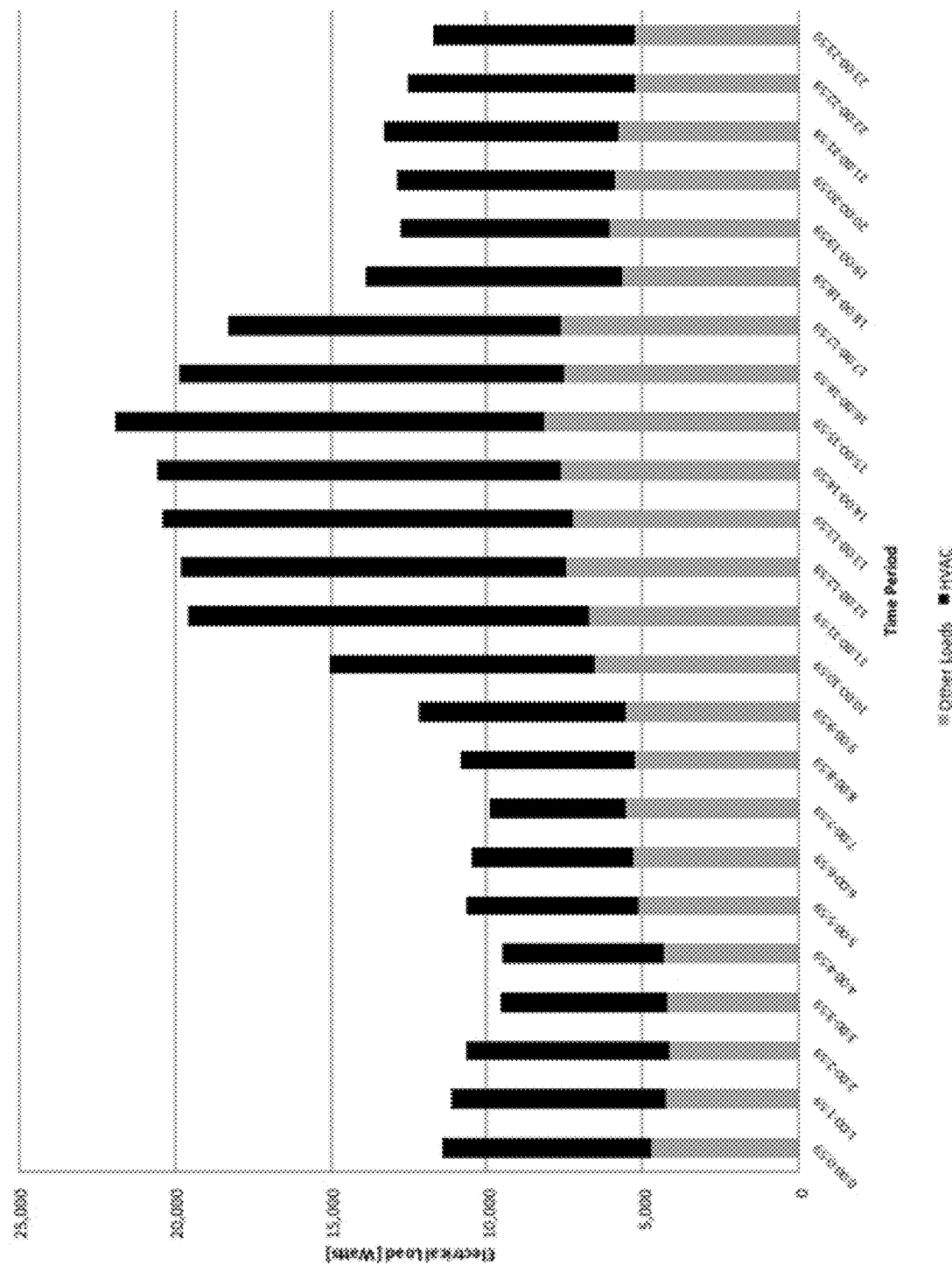
FIG. 14 is a graph of composite convention load profile measured by the microgrid assessment tool in one embodiment of the SMMS.

During testing of the SMMS, load profiles from training and deployment were similar. FIG. 14 shows the measured composite convention load profile, which is the average of the measured load profiles over five days for actual daytime operations during deployment. The deployments have large electrical usage patterns due to the heavy reliance on the HVAC system for air conditioning in hot and humid conditions.

During testing, HVAC loads were found to account for 57 percent of the load on average and varied between 44% and 66% with higher percentages between 11:00 and 17:00, when outdoor temperatures were the highest. Most medical care was performed between 16:00 and 23:00, emphasizing the fact that HVAC pulls far more power than the energy requirements of patient care.

Figure 15:
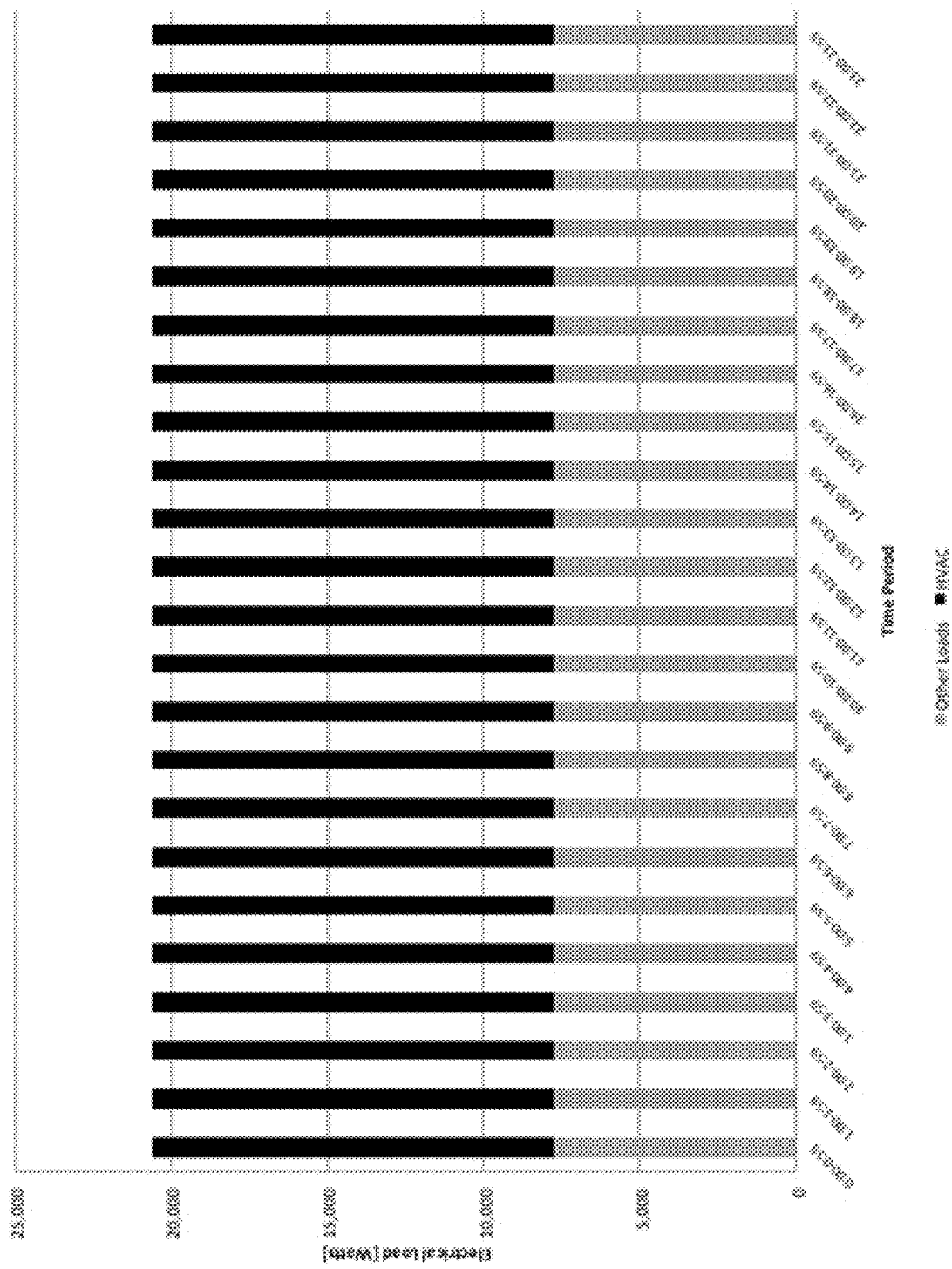
FIG. 15 is a graph of extrapolated composite convention load profile measured by the microgrid assessment tool in one embodiment of the SMMS.

FIG. 15 shows a second load model, which is an extrapolated load profile where the highest hour load was used for each hour. This represents a worst-case scenario where consistent internal heat loading was generated by staff and patients due to 24-hour operations and the exterior temperature was assumed to stay relatively constant due to humid conditions. Both were modeled to see how much of a difference the load profile would make with the 24-hour operations load profile representative of the worst case.

Figure 16:
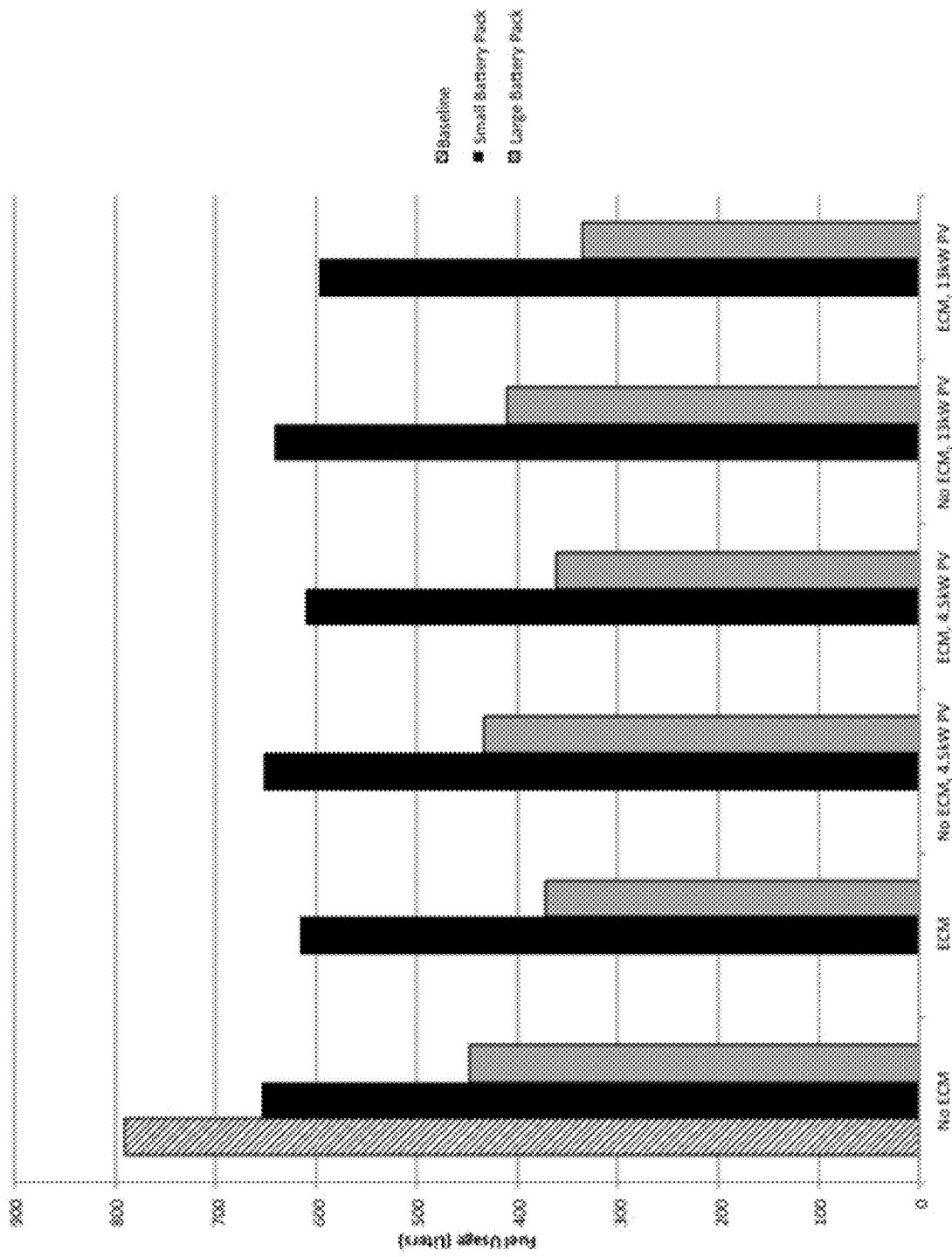
FIG. 16 is a graph that illustrates the effect of various energy conservation measures against a baseline, a small battery pack, and a large battery pack, as measured by the microgrid assessment tool in one embodiment of the SMMS.

In one exemplary embodiment of the SMMS, projections of generator run time and diesel fuel consumption may be calculated based on modeling data using various parameters. The effect of building improvements into SMMS, such as energy conservation measures, variably sized photovoltaic arrays, and battery packs may also be modeled to demonstrate the individual and cumulative benefits of these modifications. For example, FIG. 16 illustrates the effect of various energy conservation (ECM) measures against a baseline, a small battery pack, and a large battery pack.

Figure 17:
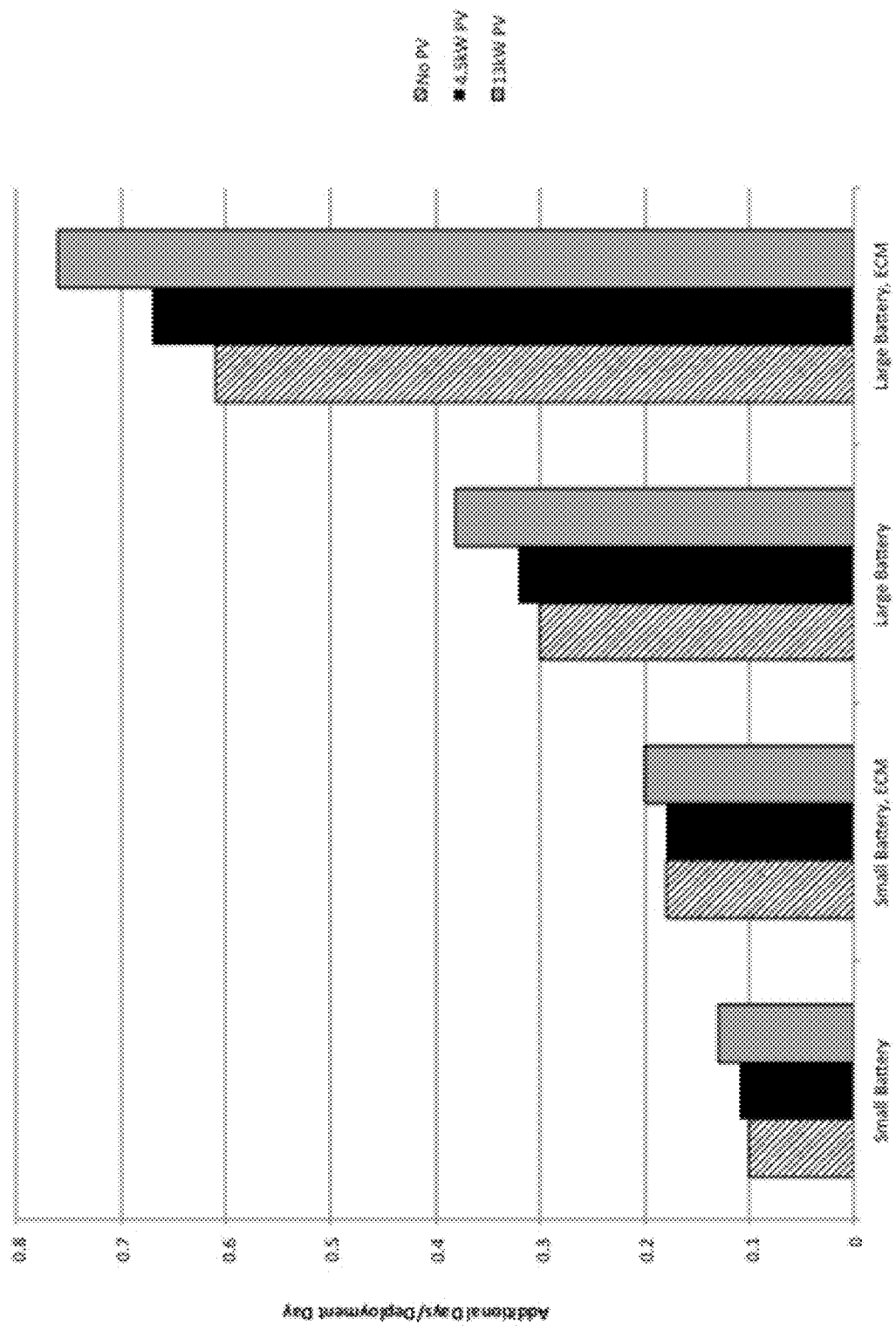
FIG. 17 is a graph of additional deployment days that can be achieved with various configurations and with and without energy conservation measures, as determined by the microgrid assessment tool in one embodiment of the SMMS.
Figure 18:
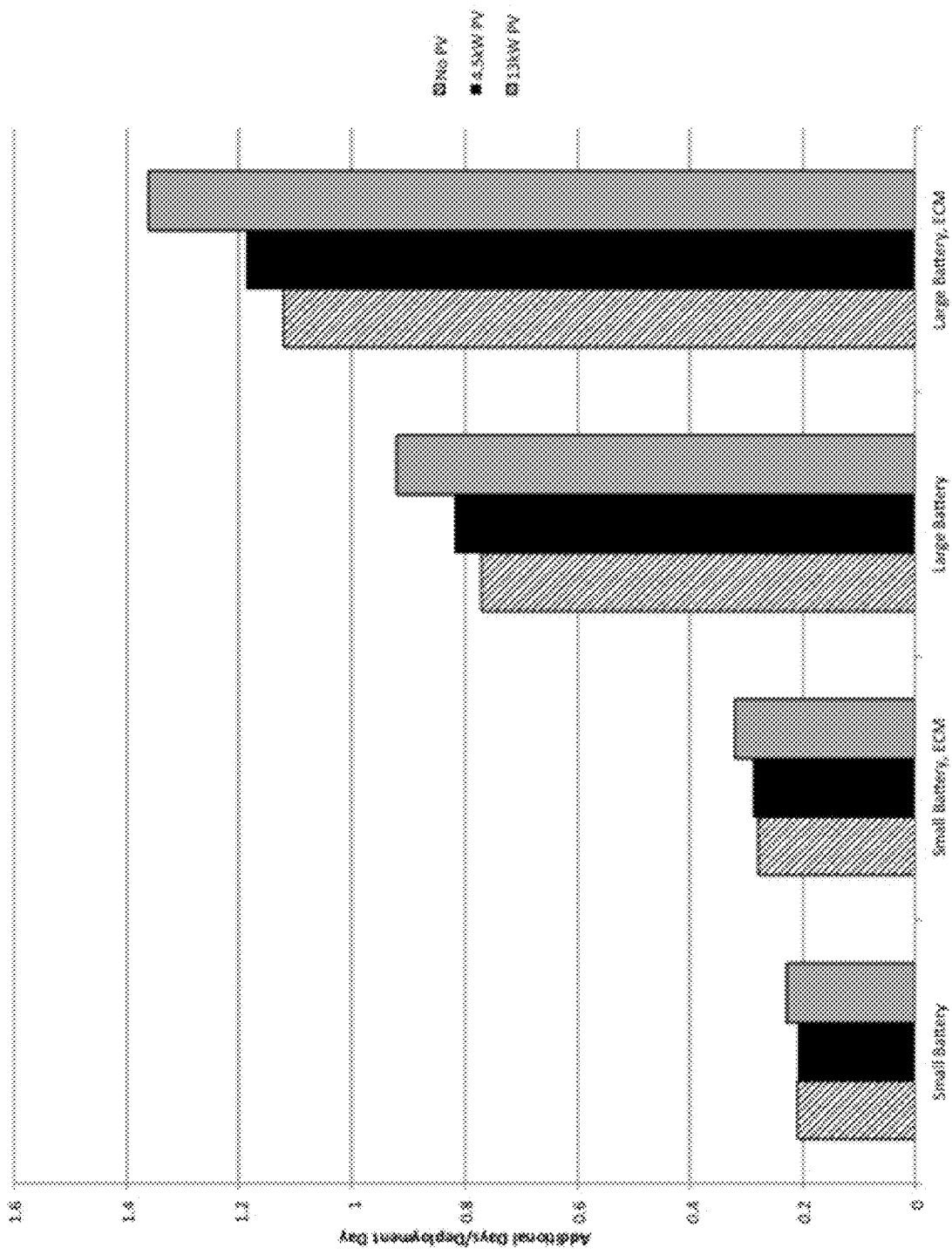
FIG. 18 is a graph of additional deployment days that can be achieved in a daytime only operation environment with various configurations and with and without energy conservation measures as determined by the microgrid assessment tool in one embodiment of the SMMS.

The results of these analyses may then be used to calculate additional days of deployment that would be possible assuming a fixed volume of fuel. Separate modeling may be performed for both 24-hour operations and daytime-only use of the SMMS. For example, as shown in FIG. 17, different configurations with and without energy conservation measures, and with various sized battery packs and photovoltaic arrays were modeled. Using a 13 kW PV array in conjunction with a large battery pack and energy conservation measures (ECM), modeling showed that for 24-hour operations, energy savings would add an additional 0.76 days/day of deployment. A similar configuration would add an additional 1.36 days/day of deployment for a daytime only operations deployment, as shown in FIG. 18.

Large-scale disasters create immediate and ongoing challenges. The disaster cycle (planning, preparedness, response and recovery) is a common framework for approaching emergency response to large scale disruptive events. During the response and recovery phases, operations focus on discrete but often overlapping phases: actions during the ongoing event (e.g. shelter, emergency care, modified search and rescue, etc.), immediate response during hours 1-48 (e.g. rapid needs assessment, gap analysis, provision of emergency care, etc.), and acute response and recovery during days 2-14 (e.g. provision of emergency care, reestablishment of local health care infrastructure and transition to local resources, etc.).

Reliable energy is core to all phases of disaster response. Disruption of the power grid, loss of water and sewage systems, disabled communication infrastructure, and interruption of routine logistics impede disaster response and emergency medical care. Research has shown that all-cause mortality increases during severe power outages. Several recent natural disasters demonstrate the fragility of our infrastructure and our reliance on fossil fuels. During "Superstorm" Sandy, NYU's Langone Medical Center lost primary power and had inoperable back up roof-mounted reserve generators. The Medical Center was forced to evacuate the entire hospital and transfer multiple critically ill patients on advanced life-support. Two weeks after the storm, power remained unreliable or absent. The Federal Emergency Management Agency (FEMA) was able to provide reliable diesel fuel for Federal response assets, distributing 313,000 gallons of gasoline and 157,000 gallons of diesel fuel in the first two weeks. However, civilian entities were less fortunate and individuals were often forced to wait in line for up to 16 hours for gasoline.

The tornado in Joplin Mississippi in 2011 is another recent example of the fragility of medical and community infrastructure. The tornado flattened a one-mile by six-mile path through downtown that affected the local hospital, nursing homes, schools, and houses. Nearly 35% of the population was without power. During the storm an emergent surgical case had to be performed by flashlight. A deployable, integrated microgrid system, as described in connection with the SMMS circumvents the need for this austerity, allow critical operations to continue normally, which dramatically improves community health.

There are four critical concerns for response operations in the aftermath of a storm such as Sandy: 1) identifying and treating casualties requiring urgent intervention, 2) minimizing public-health risks caused by flooding, 3) restoring essential supply chains, and 4) providing access to care. Provision of reliable power is critical to achieving all of the critical concerns ranging from powering triage and staging tents, to running water purification systems, to shifting the logistics burden from providing fuel to providing medications or shelter.

In the aftermath of Katrina, a mobile medical fleet cared for thousands of patients and demonstrated its capabilities at providing access to care when existing health care institutions were suddenly off line. However, this mobile medical fleet's technologically advanced care capabilities were still reliant on diesel fuel re-supply. The capacity of distributed generation through the implementation of the SMMS microgrid allows mobile medical fleets to provide immediate and sustained tertiary-care during the ongoing and immediate post disaster phase. Integrated into a larger response, the SMMS will require less fuel and less water, reducing the strain on external logistics and resupply efforts. The SMMS microgrid energy optimization capabilities would have been invaluable in directly addressing a majority of the critical concerns detailed in the post-Hurricane Katrina and post-Hurricane Sandy after-action reports.

Although small-scale efforts have been made in the past to use solar power in disaster and emergency response, the SMMS is the first system capable of using an integrated microgrid for powering advanced medical care post disaster. The SMMS provides a comprehensive energy strategy that incorporates energy conservation measures, power storage, and smart energy utilization through microgrid technology to provide advanced medical care in austere environments.

In one embodiment, energy usage by the SMMS may be sensitive to the generator minimum loading ratio (MLR). This sensitivity is most pronounced in the scenarios using the daytime operations load profile. This makes sense as measured loads varied from under 10 kW to just over 20 kW each day. This means that only a third of the fuel being consumed by the generator is used to directly power the loads during the low usage time periods assuming a 30% MLR. A 30% MLR means that all loads below 30 kW consume the same amount of fuel when using a 100 kVA generator. This fraction of fuel used to directly power loads may increase around 66% when the MLR is assumed to be 15%. When battery storage is added to build out a microgrid, the excess electricity from the generator, (the electricity that is not used directly by power loads—HVAC, lighting, equipment, etc.) is captured and stored in the batteries for later use. This storage allows the generator to turn off periodically and transition to the batteries to satisfy loads. In other words, the microgrid allows the generator to be used most efficiently.

The results also show that integrating a modern battery array into the microgrid has a larger impact for fuel savings than either energy conservation measures or adding a photovoltaic array. This observation makes sense since neither efficiency measures nor photovoltaic generation will cut fuel consumption if the generator loads are already below the minimum load ratio. The efficiency measures and photovoltaic array make a difference in fuel consumption when batteries are added. By lowering the net load, energy conservation measures would increase the time the generator could be off due to decreased battery discharge rates. Photovoltaic arrays may also increase generator downtime by providing an alternate source of energy to the batteries. A microgrid may be necessary to handle these alternate power routes, but would yield the distinct advantage of increasing operational time.

Using SMMS, disaster response operation times could be more than doubled before refueling is required through the incorporation of a 450 kWh battery bank and a 13.5 kW PV array. This capability allows the SMMS to extend time on station while decreasing reliance on local (and perhaps scarce) resources. This independence in turn leads to greater resilience and the possibility of operating in more austere environments. Using distributive generation allows for greater flexibility of the SMMS as it permits the incorporation of solar, wind, biodiesel or any other suitable fuel source. Having such a robust and efficient generation system also allows the SMMS to act as a short-term power utility (i.e. power plant) for other operations in the immediate vicinity. The microgrid used in the SMMS significantly increases autonomy and resiliency during disaster operations. The improved energy efficiency of the SMMS that couples energy conservation measures and microgrid technology has clear operational, financial, and environmental benefits. The SMMS is a fully integrated energy management system that is more flexible, independent, and resilient than previous systems, while being cheaper and cleaner to operate.

Although certain portions of this disclosure may relate to healthcare or disaster recovery management, it will be understood that the concepts can be easily applied to other fields with little or no modification. Also, while certain implementations relate to energy technology, the concepts can be implemented to other fields, for example, communication technology to create mobile internet units to provide wireless coverage in disaster areas.

This disclosure and the accompanying figures illustrate various non-limiting, exemplary, inventive aspects of the SMMS. It should be appreciated by those skilled in the art that any figures represent conceptual views of illustrative systems. Similarly, it should be appreciated that any flow charts, flow diagrams, state transition diagrams, pseudo code, and the like represent various processes, which may be substantially represented in a computer readable medium and so executed by a computer or processor, whether or not such computer or processor is explicitly shown.

The order in which the various methods described in this disclosure is not intended to be construed as a limitation, and any number of the described method steps can be combined in any order to implement the methods, or an alternative method. Additionally, individual steps may be deleted from or added to the methods described in this disclosure without departing from the scope of the subject matter. Furthermore, the methods can be implemented in any suitable hardware, software, firmware, or combination thereof. The methods may also be taught to a user through written, pictographic, audio or audiovisual instructions.

The invention claimed is:

1. A method for energy management in a mobile medical unit, the method comprising:
   using a microgrid assessment tool to capture both granular load profiles and power quality data for a mobile medical unit powered by a microgrid;
   modeling a plurality of scenarios, using the data captured by the microgrid assessment tool to determine hybrid power system optimization; and
   supplying power to the mobile medical unit from one or more of a plurality of energy sources in the hybrid microgrid based on the results of the optimization;
   detecting at predefined time intervals whether the power supplied by the plurality of energy sources is greater than a threshold value,
   wherein the threshold value is determined based on the modeling of the plurality of scenarios, and
   wherein the plurality of energy sources includes at least one renewable energy source and at least one non-renewable energy source.

2. The method of claim 1, wherein the microgrid assessment tool comprises a base station and an embedded datalogger.

3. The method of claim 1, wherein the microgrid assessment tool comprises a battery and a photovoltaic module for charging the battery.

4. The method of claim 1, further comprising diverting energy above the threshold to an energy storage system within the hybrid microgrid.

5. The method of claim 1, wherein input parameters for the modeling include at least one of photovoltaic array size, power converter capacity, battery bank size, load profiles, generator minimum load ratio, efficiency, and solar resource available.

6. The method of claim 1, wherein the renewable energy sources are at least one of solar, wind, geothermal, hydroelectric, wave, and biomass devices.

7. The method of claim 1, wherein the non-renewable energy source is a diesel generator.

8. The method of claim 1, wherein modeling comprises estimating fuel savings due to energy storage.

9. The method of claim 1, wherein the non-renewable energy source is a generator and the minimum loading ratio of the generator functions as a modeling input.

10. The method of claim 3, wherein the battery is a battery bank having a capacity between 90 kWh and 450 kWh.

11. The method of claim 3, wherein the battery is a battery bank having a capacity of approximately 450 kWh.

12. The method of claim 3, wherein the photovoltaic array has an output between 4.5 kW and 13.5 kW.

13. The method of claim 3, wherein the photovoltaic array has an output between 9 kW and 13.5 kW.

14. The method of claim 3, wherein the photovoltaic array has an output of approximately 13.5 kW.

15. The method of claim 3, wherein the battery bank has a capacity of approximately 450 kWh and the photovoltaic array is capable of producing approximately 13.5 kW.

16. The method of claim 2, wherein the microgrid assessment tool further comprises a second-class pyranometer for measuring solar resource.

17. The method of claim 16, wherein the microgrid assessment tool further comprises a weather station configured to measure and transmit wind speed, wind direction, precipitation, ambient temperature, relative humidity, and barometric pressure.

18. The method of claim 1, wherein a mobile medical system includes:
   the mobile medical unit; and
   the hybrid microgrid configured to provide power to the mobile medical unit;
   wherein the hybrid microgrid further comprises:
      a measurement-and-verification module, and
      at least one energy storage device.

19. The method of claim 18, wherein the hybrid microgrid is further configured to receive data from the measurement-and-verification module and regulate the use of the generator and the renewable energy source to maximize generator efficiency.

20. The method of claim 18, wherein the hybrid microgrid is further configured to function as a power utility to provide power to other operations in the vicinity of the mobile medical unit.

21. The method of claim 18, wherein the hybrid microgrid is further configured to capture excess energy that is not used directly by power loads in the mobile medical unit and store that energy in the energy storage device for later use.

22. The method of claim 18, wherein the energy storage device is a battery bank.

23. The method of claim 18, wherein the renewable energy source is a photovoltaic solar array.

24. The method of claim 18, wherein the non-renewable energy source is a generator.

25. The method of claim 18, wherein the mobile medical unit is a mobile ground unit, and wherein the measurement-and-verification module includes the microgrid assessment tool.

26. The method of claim 18, wherein the mobile medical unit is a mobile container unit, the mobile container unit includes a collapsible container.

27. The method of claim 18, wherein the mobile medical unit is configured to function as at least one of a laboratory, a triage facility, an operating room, a morgue, a pharmacy, medical housing, a nursing station, and a laundry facility.

* * * * *

UNITED STATES PATENT AND TRADEMARK OFFICE
CERTIFICATE OF CORRECTION

PATENT NO. : 12,230,967 B2
APPLICATION NO. : 14/920743
DATED : February 18, 2025
INVENTOR(S) : Kevon R. Makell et al.

Page 1 of 1

It is certified that error appears in the above-identified patent and that said Letters Patent is hereby corrected as shown below:

In the Claims

Claim 1, Column 13, Line 47, replace "powered by a microgrid" with "powered by a hybrid microgrid"

Signed and Sealed this
Fifteenth Day of April, 2025

Coke Morgan Stewart
*Acting Director of the United States Patent and Trademark Office*